US009592111B2

(12) United States Patent
 Groh

(10) Patent No.: US 9,592,111 B2
(45) Date of Patent: Mar. 14, 2017

(54) VALVE REPLACEMENT DEVICES

(71) Applicant: Mark Groh, Fairview, NC (US)

(72) Inventor: Mark Groh, Fairview, NC (US)

( * ) Notice: Subject to any disclaimer, the term of this patent is extended or adjusted under 35 U.S.C. 154(b) by 0 days.

(21) Appl. No.: 15/143,079

(22) Filed: Apr. 29, 2016

(65) Prior Publication Data

US 2016/0317276 A1 Nov. 3, 2016

Related U.S. Application Data

(60) Provisional application No. 62/155,002, filed on Apr. 30, 2015.

(51) Int. Cl.
  *A61F 2/24* (2006.01)
  *A61F 2/01* (2006.01)

(52) U.S. Cl.
  CPC ............. *A61F 2/013* (2013.01); *A61F 2/2427* (2013.01); *A61F 2002/011* (2013.01); *A61F 2002/016* (2013.01)

(58) Field of Classification Search
  CPC .......... A61F 2/24; A61F 2/013; A61F 2/2436; A61M 1/3653; A61M 1/3664; A61M 1/3659
  See application file for complete search history.

(56) References Cited

U.S. PATENT DOCUMENTS

| | | | |
|---|---|---|---|
| 4,873,978 A | 10/1989 | Ginsburg | |
| 5,662,671 A | 9/1997 | Barbut et al. | |
| 5,769,816 A | 6/1998 | Barbut et al. | |
| 5,993,469 A | 11/1999 | McKenzie et al. | |
| 6,287,321 B1 | 9/2001 | Jang | |
| 7,344,515 B2 | 3/2008 | Coyle | |
| 8,323,327 B2 | 12/2012 | Bei et al. | |
| 8,372,108 B2 | 2/2013 | Lashinski | |
| 8,430,902 B2 | 4/2013 | Bergheim | |
| 8,518,073 B2 | 8/2013 | Lashinski | |
| 8,753,370 B2 | 6/2014 | Lashinski | |
| 2005/0137696 A1 | 6/2005 | Salahieh et al. | |
| 2009/0163846 A1 | 6/2009 | Aklog et al. | |
| 2013/0131787 A1* | 5/2013 | Ginn ................. | A61M 25/1002 623/2.1 |
| 2013/0253571 A1 | 9/2013 | Bates | |
| 2014/0018912 A1 | 1/2014 | Delaloye et al. | |

(Continued)

OTHER PUBLICATIONS

Kereiakes, Dean J., MD et al, "A Novel Filter-Based Distal Embolic Protection Device for Percutaneous Intervention of Saphenous Vein Graft Lesions," JACC: Cardiovascular Interventions, vol. 1, No. 3, 2008.

(Continued)

*Primary Examiner* — Victor Nguyen
(74) *Attorney, Agent, or Firm* — Kilpatrick Townsend & Stockton LLP

(57) ABSTRACT

An embolic material blocking catheter includes a handle assembly, an elongated element having a lumen, and a deployable embolic material blocking element. The embolic material blocking catheter is configured to accommodate insertion of a treatment catheter into the lumen to position a treatment device distal to the embolic material blocking element for administering a treatment at a treatment site and/or convey embolic material blocked by the embolic material blocking element for extraction from the patient.

8 Claims, 25 Drawing Sheets

(56) References Cited

U.S. PATENT DOCUMENTS

| | | |
|---|---|---|
| 2014/0067050 A1 | 3/2014 | Costello et al. |
| 2014/0277096 A1 | 9/2014 | Richter et al. |

OTHER PUBLICATIONS

Nietlispach, Fabian, MD, et al., "An Embolic Deflection Device for Aortic Valve Interventions," JACC: Cardiovascular Interventions, vol. 3, No. 11, 2010.

Desai, Chintan S., MD et al., "Transcatheter Valve Replacement for Aortic Stenosis, Balancing Benefits, Risks, and Expectations," JAMA, vol. 308, No. 6, Aug. 8, 2012.

Eggebrecht, Holger, MD, et al., "Risk of Stroke After Transcatheter Aortic Valve Implantation (TAVI): A Meta-Analysis of 10,037 Published Patients," EuroIntervention, vol. 8, pp. 129-138, 2012.

"Embolic Protection Devices," Endovascular Today, 2012 Buyer's Guide.

Mack, Michael J., MD, et al., "Outcomes Following Transcatheter Aortic Valve Replacement in the United States," JAMA, vol. 310 (19), pp. 2069-2077, 2013.

Werner, Martin, MD, et al., "First Clinical Experience With the GARDEX EPD: a Novel Embolic Protection Device for Carotid Artery Stenting," EuroIntervention, vol. 8, pp. 1026-1032, 2013.

Ye, Jian, MD, FRCSC, "Cerebral Embolic Protection During TAVI," TAVI Summit Korea 2013.

Russo, Mark, MD, et al., "Trans-Aortic Transcatheter Aortic Valve Replacement with Edwards Sapier Ascendra 3," CTSNet, The Cardiothoracic Surgery Network, Oct. 10, 2014.

Groh, Mark A., MD et al., "Transaortic Approach: Impact on Clinical Outcomes for Patients Receiving Transcatheter Aortic Valve Replacement (TAVR)," $51^{st}$ STS Meeting, San Diego, CA, Jan. 24-28, 2015.

Ford, Omar, "Keystone Heart's TriGuard Lowers Risk of Stroke for TAVR Patients" Medical Device Daily, American College of Cardiology Scientific Session 2015, vol. 19, No. 53, p. 1; p. 9, Mar. 18, 2015.

* cited by examiner

VALVE REPLACEMENT DEVICES

CROSS-REFERENCES TO RELATED APPLICATIONS

This application claims the benefit of U.S. Provisional Application No. 62/155,002, filed Apr. 30, 2015, which is incorporated herein by reference in its entirety for all purposes.

BACKGROUND

Transcatheter aortic valve replacement (TAVR) is a proven strategy for the treatment of severe aortic stenosis that has been validated for use in patients who are not eligible for surgical aortic valve replacement (SAVR) due to patient frailty or associated high operative risk. TAVR with the use of a self-expanding or balloon-expanded bioprosthetic valve has been FDA-approved for commercial use in the US in selected patients. TAVR is rapidly becoming the method of choice to treat aortic stenosis in patients deemed to be at increased risk of death if offered a traditional surgical aortic valve replacement. Patients presently selected for TAVR, however, are most often elderly with frailty and a number of comorbidities. The femoral artery is generally the first choice for access to the aortic valve. In patients with significant arterial occlusive disease, however, marked tortuosity of the ileo femoral system and/or significant at risk atheromatous plaque within the native aorta and/or aneurysmal disease may present significant risk for femoral access such that alternate access TAVR is preferable. An alternative route has been proposed several years ago in the form of a trans-apical (TA) approach through the apex of the left ventricle exposed through a left lateral thoracotomy. The TA approach, however, requires opening the left chest in patients having potential pulmonary dysfunction and the rate of bleeding complications may be higher than that observed after traditional trans-femoral (TF) approach. In the search for yet another alternative to compromised peripheral arterial vascular access, a direct trans-aortic (TAo) route has been described in a limited number of cases since 2010. In a recent report, the cases performed through a TAo route represented only 4% of the TAVR cases performed by 2013.

Although results have been encouraging with TAVR, the risk of stroke has been demonstrated to be significantly higher with TAVR relative to SAVR. Clinically observed stroke (CVA) underestimates the prevalence of embolic events inherent with TAVR. During TAVR, stent and implanted valve expansion (with or without the use of a balloon) results in native valve compression and radial leaflet displacement that leads to the liberation of tissue and particulate matter that travels distally in the arterial tree. Some of the debris lodges in terminal branches of cerebral vessels and will be evidenced with new onset stroke. Other debris released at the time of TAVR lodge in vessels of the peripheral circulation, renal circulation, coronary circulation, and mesenteric circulation. These patients may manifest clinical scenario of renal failure, mesenteric ischemia, peripheral ischemia, and/or myocardial infarction. Other patients may not have acute clinical deterioration but may suffer late effects due to impaired functional reserve related to sub-clinical embolic events. The occurrence of embolic events during TAVR is a significant impediment to offering the technique to larger lower risk groups of patients.

A number of different approaches have been developed for embolic prevention. Existing embolic prevention devices are primarily directed to deflect embolic material from the brachiocephalic vessels or capture embolic material within the brachiocephalic vessels. There are a number of difficulties with these existing embolic prevention devices. First, deployment of the devices requires additional time and can conflict with the performance of the valve procedure. Second, deployment of the devices may lead to additional vessel trauma and liberation of embolic material. Third, the deployment of the devices may be difficult and stability of deployment may make protection less than reliable. Fourth, the devices do not protect the brain from all sources of blood flow and particularly posterior cerebral blood flow is not filtered. Fifth, systemic embolization will still occur that may lead to intestinal, renal, and/or peripheral manifestations of ischemic gut, renal insufficiency and/or peripheral ischemia. Sixth, coronary embolization and myocardial infarction may occur due to proximal embolization.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

An embolic material blocking catheter includes an integrated embolic material blocking element that is deployable within a blood vessel downstream of a treatment site to block embolic material released from the treatment site from flowing downstream through the blood vessel, thereby preventing associated embolism(s). For example, the integrated embolic material blocking element can be deployed in a patient's aorta downstream of the patient's aortic valve to block flow of embolic material released during implantation of a prosthetic aortic valve. In many embodiments, the embolic material blocking catheter includes a lumen into which a delivery catheter for the prosthetic valve can be inserted to advance the prosthetic valve to a implantation site upstream of the deployed embolic material blocking element. In many embodiments, the lumen is configured to accommodate extraction of embolic material blocked by the embolic material blocking element while also accommodating the delivery catheter. The embolic material blocking catheter and related delivery catheter, devices, and methods are especially suited for use in TAVR via any access (including, but not limited to, femoral, direct aortic access, brachiocephalic, subclavian, axillary or carotid arteries), which enables accurate positioning of the prosthetic aortic valve.

Thus, in one aspect, a system is provided for implanting a prosthetic aortic valve into a patient. The system includes an embolic material blocking catheter and a delivery catheter. The embolic material blocking catheter includes a handle assembly, an elongated element, and an embolic material blocking element. The elongated element has a proximal portion coupled with the handle assembly, a distal portion, and a lumen extending through the distal portion. The embolic material blocking element is connected to the distal portion of the elongated element. The embolic material blocking catheter is reconfigurable from a first configuration in which the embolic material blocking element is in an insertion configuration to a second configuration in which the embolic material blocking element is in a deployed configuration. The embolic material blocking catheter is reconfigurable from the second configuration to a third configuration in which the embolic material blocking element is in a captured configuration. The first configuration of the embolic material blocking catheter accommodates insertion of the distal portion of the elongated element and the embolic material blocking element into the aorta downstream of an implantation site for the prosthetic aortic valve. The deployed configuration of the embolic material blocking element has an outer circumference adapted to interface with the inner surface of the aorta and blocks flow of embolic material through the aorta past the embolic material blocking element. The third configuration accommodates removal of the distal portion of the elongated element and the embolic material blocking element from the patient. The delivery catheter is configured to deploy the prosthetic aortic valve. The delivery catheter is configured to be advanced through the lumen of the elongated element of the embolic material blocking catheter to position the prosthetic aortic valve upstream of the embolic material blocking element for deployment. The delivery catheter includes a deployment mechanism adapted to deploy the prosthetic aortic valve from a pre-deployment configuration.

The deployment mechanism can have any suitable configuration for deploying the prosthetic valve from the pre-deployment configuration. For example, the deployment mechanism can include an expandable member (e.g., an inflatable balloon) configured to deploy the prosthetic aortic valve by expanding the prosthetic aortic valve from the pre-deployment configuration. As another example, the deployment mechanism can include a sheath configured to restrain a self-expanding prosthetic aortic valve in the pre-deployment configuration and articulable relative to the self-expanding prosthetic aortic valve in the pre-deployment configuration to release the prosthetic aortic valve to accommodate self-expansion of the prosthetic aortic valve.

In many embodiments, the embolic material blocking catheter is reconfigurable from a configuration suitable for insertion of the embolic material blocking catheter to a deployed configuration, and from the deployed configuration to a configuration suitable for removal of the embolic material blocking catheter. For example, the embolic material blocking catheter can include an articulable sheath repositionable from a first position adapted to retain the embolic material blocking element in the insertion configuration to a second position accommodating reconfiguration of the embolic material blocking element to the deployed configuration. The articulable sheath can be articulable from the second position to a third position to capture the embolic material blocking element.

The embolic material blocking element can have any suitable configuration for blocking downstream flow of embolic material. For example, the embolic material blocking element can include a filtering membrane adapted to remove embolic material from blood flowing through the aorta.

In many embodiments, the embolic material blocking catheter is configured to enable removal of embolic material from the patient. For example, the handle assembly can include an embolic material extraction port in fluid communication with the lumen of the elongated element. The lumen of the elongated element can be configured to transport embolic material that is diverted by the embolic material blocking element to the embolic material extraction port. The embolic material extraction port can be configured to be placed in fluid communication with an embolic material extraction device operable to receive embolic material from the lumen through the embolic material extraction port. In many embodiments, the system for implanting a prosthetic valve includes the embolic material extraction device.

In many embodiments, the embolic material blocking element is configurable to guide embolic material to the lumen of the elongated element for removal from the patient through the lumen. For example, in many embodiments the embolic material blocking element is configurable to extend downstream from an outer circumference of the embolic material blocking element to an inner circumference of the embolic material blocking element that is coupled with the elongated element so as to guide embolic material diverted by the embolic material blocking element to the lumen for transport through the lumen for removal via the embolic material extraction port.

In many embodiments, the embolic material blocking catheter includes an insertion port for the delivery catheter. For example, the insertion port can be configured to accommodate insertion of a distal portion of the delivery catheter supporting the prosthetic valve in the pre-deployment configuration into the lumen of the elongated element and advancement of the distal portion of the delivery catheter through the lumen to position the prosthetic aortic valve upstream of the embolic material blocking element for deployment from the pre-deployment configuration. In many embodiments, the insertion port is configured to inhibit leakage from the lumen.

In another aspect, a method is provided for implanting a prosthetic aortic valve in a patient. The method includes supporting an embolic material blocking element in an insertion configuration via a distal portion of an embolic material blocking catheter. The distal portion of the embolic material blocking catheter is advanced into the patient's aorta. The embolic material blocking element is expanded from the insertion configuration to a deployed configuration having an outer circumference interfaced with an inner surface of the patient's aorta to substantially block flow of embolic material through the patient's aorta past the embolic material blocking element. The prosthetic aortic valve is supported in a pre-deployed configuration via a distal portion of a delivery catheter. The distal portion of the delivery catheter and the prosthetic valve in the pre-deployment configuration are advanced through a lumen of the embolic material blocking catheter to position the prosthetic valve in the aorta upstream of the embolic material blocking element in the deployed configuration. The delivery catheter is reconfigured to deploy the prosthetic aortic valve upstream of the embolic material blocking element in the deployed configuration.

Any suitable approach can be used to deploy the embolic material blocking element. For example, in many embodiments of the method, expanding the embolic material blocking element from the insertion configuration to the deployed configuration includes proximally retracting a retaining sheath of the embolic material blocking catheter relative to the embolic material blocking element to release the embolic material blocking element from constraint imposed by the retaining sheath.

The delivery catheter can be removed from the patient prior to removing the embolic material blocking catheter from the patient. For example, the method can include removing the delivery catheter from the patient through the lumen of the embolic material blocking catheter. The embolic material blocking catheter can then be reconfigured to reconfigure the embolic material blocking element from the deployed configuration to a captured configuration. The embolic material blocking catheter can be removed from the patient with the embolic material blocking element in the captured configuration.

Many embodiments of the method includes removing embolic material from the patient. For example, the method can include operating an embolic material extraction device in fluid communication with the lumen of the embolic material blocking catheter to extract embolic material from the patient diverted by the embolic material blocking element.

Any suitable insertion route for the embolic material blocking catheter can be used. For example, inserting the distal portion of the embolic material blocking catheter into the aorta can employ a direct access trans-aortic (TAo) route. As another example, inserting the distal portion of the embolic material blocking catheter into the aorta can include routing the distal portion of the embolic material blocking catheter through the femoral artery, the carotid artery, the axillary artery, or a brachiocephalic artery.

In another aspect, an embolic material blocking catheter is provided. The embolic material blocking catheter includes a handle assembly, an elongated element having a proximal portion coupled with the handle assembly, and an embolic material blocking element. The elongated element has a distal portion and a lumen extending through the distal portion. The embolic material blocking element is coupled to the distal portion of the elongated element. The embolic material blocking catheter is reconfigurable from a first configuration in which the embolic material blocking element is in an insertion configuration to a second configuration in which the embolic material blocking element is in a deployed configuration. The embolic material blocking catheter is reconfigurable from the second configuration to a third configuration in which the embolic material blocking element is in a captured configuration. The insertion configuration accommodates insertion of the distal portion of the elongated element and the embolic material blocking element into a blood vessel of a patient to position the embolic material blocking element downstream of a treatment site. The deployed configuration of the embolic material blocking element has an outer circumference adapted to interface with the inner surface of the blood vessel and blocks flow of embolic material through the blood vessel past the embolic material blocking element. The third configuration accommodates removal of the distal portion of the elongated element and the embolic material blocking element from the patient. The lumen of the elongated element is configured to one or both of: (a) accommodate insertion of a treatment catheter into the lumen to position a treatment device mounted to the treatment catheter distal to the embolic material blocking element in the deployed configuration for administering a treatment at the treatment site, or (b) convey embolic material blocked by the embolic material blocking element away from the embolic material blocking element in the deployed configuration for extraction from the patient.

In many embodiments, the embolic material blocking catheter includes an articulable sheath for restraining, deploying, and capturing the embolic material blocking element. For example, the embolic material blocking catheter can include an articulable sheath repositionable from a first position adapted to retain the embolic material blocking element in the insertion configuration to a second position accommodating reconfiguration of the embolic material blocking element to the deployed configuration. The articulable sheath can be repositionable from the second position to a third position restraining the embolic material blocking element in the captured configuration.

The embolic material blocking element of the embolic material blocking catheter can have any suitable configuration. For example, the embolic material blocking element can include a filtering membrane adapted to remove embolic material from blood flowing through the blood vessel.

Many embodiments of the embolic material blocking catheter are configured for removal of embolic material from the patient. For example, the handle assembly can include an embolic material extraction port in fluid communication with the lumen of the elongated element. In many embodiments, the lumen of the elongated element is configured to transport embolic material that is diverted by the embolic material blocking element to the embolic material extraction port. In many embodiments, the embolic material extraction port is configured to be placed in fluid communication with an embolic material extraction device operable to receive embolic material from the lumen through the embolic material extraction port. In many embodiments, the embolic material blocking catheter includes the embolic material extraction device.

For a fuller understanding of the nature and advantages of the present invention, reference should be made to the ensuing detailed description and accompanying drawings.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
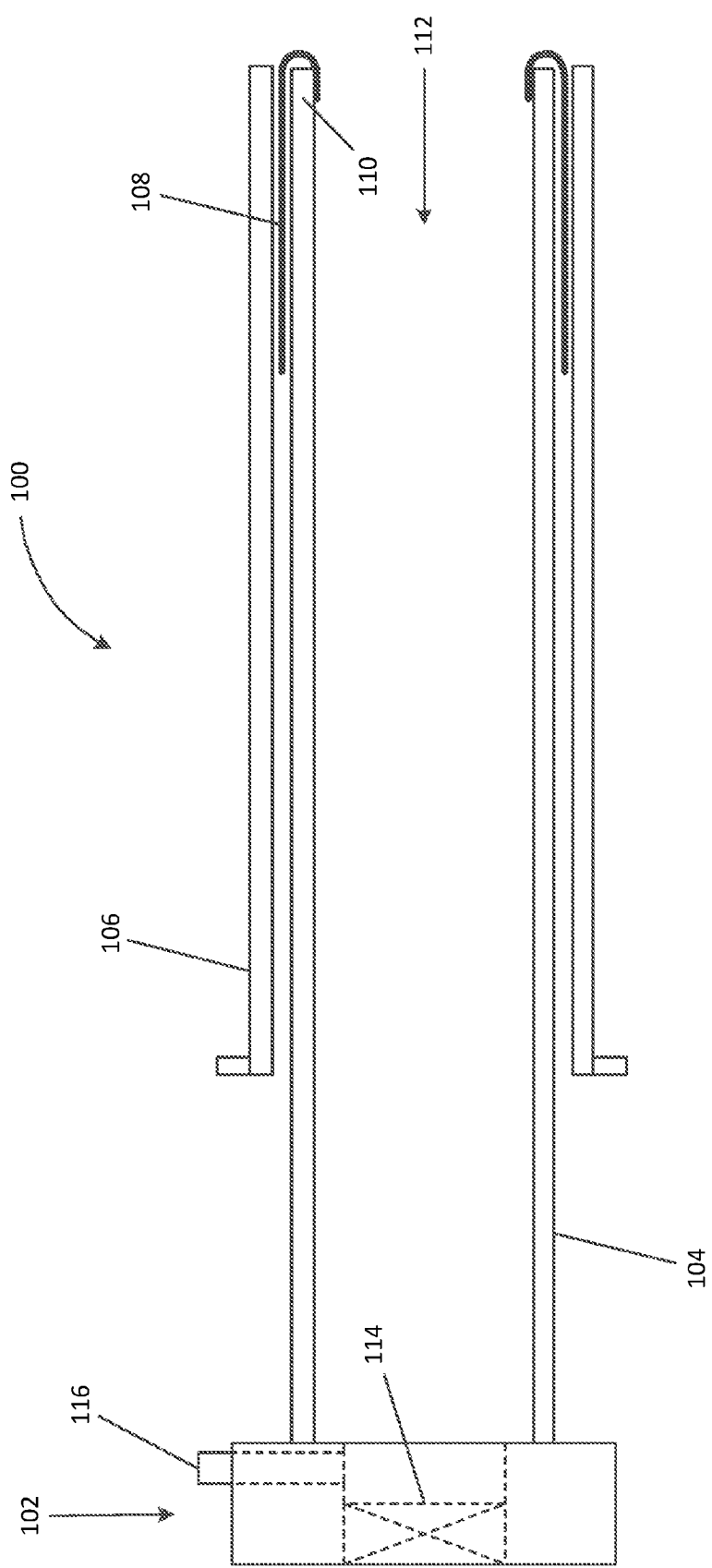
FIG. 1 illustrates an embolic material blocking catheter in an insertion configuration, in accordance with many embodiments.

Referring now to the drawings, in which like reference numerals represent like parts throughout the several views, FIG. 1 is a simplified schematic drawing illustrating an embolic material blocking catheter 100 in an insertion configuration suitable for insertion into a blood vessel of a patient via any suitable insertion route, in accordance with many embodiments. The embolic material blocking catheter 100 includes a handle assembly 102, an elongated main tube 104, a retention sleeve 106, and a deployable embolic material blocking element 108. The embolic material blocking element 108 has an inner circumference that is attached to a distal portion 110 of the elongated main tube 104. In the insertion configuration shown, the embolic material blocking element 108 is restrained in a collapsed configuration between the retention sleeve 106 and the elongated main tube 104. As described herein, deployment of the embolic material blocking element 108 is accomplished via a proximal retraction of the retention sleeve 106 to release the embolic material blocking element 108 from the constraint provided by the retention sleeve 106. The elongated main tube 104 has a central lumen 112 through which a treatment catheter can be deployed and/or embolic material can be extracted.

In the illustrated embodiment, the handle assembly 102 is connected to the elongated main tube 104 and includes an insertion port 114 and an embolic material extraction port 116. In many embodiments, the insertion port 114 is configured to accommodate insertion of a treatment catheter through the insertion port 114 into the lumen 112 for advancement to a treatment site distal to the embolic material blocking element 108 while inhibiting escape of patient fluid (e.g., blood) from the lumen 112. For example, the insertion port 114 can include a diaphragm valve configured to block the escape of patient fluid when no treatment catheter is inserted through the insertion port 114 and interface with a treatment catheter to block escape of blood from the lumen 112 around the treatment catheter when the treatment catheter is inserted through the insertion port 114. The embolic material extraction port 116 is in fluid communication with the lumen 112 and configured for transfer of embolic material from the lumen 112. For example, the embolic material extraction port 116 can be configured to be placed in fluid communication with a suitable embolic material extraction device (e.g., a suitable pump, a suitable syringe), which can be operable to receive embolic material and/or patient fluid from the lumen 112 via the embolic material extraction port 116.

In many embodiments, the embolic material blocking catheter 100 is configured for use in intercepting embolic material released within a blood vessel of a patient during any suitable treatment procedure. Applicable treatment procedures include, but are not limited to, treatments referred to herein such as the implantation of a prosthetic aortic valve.

Figure 2:
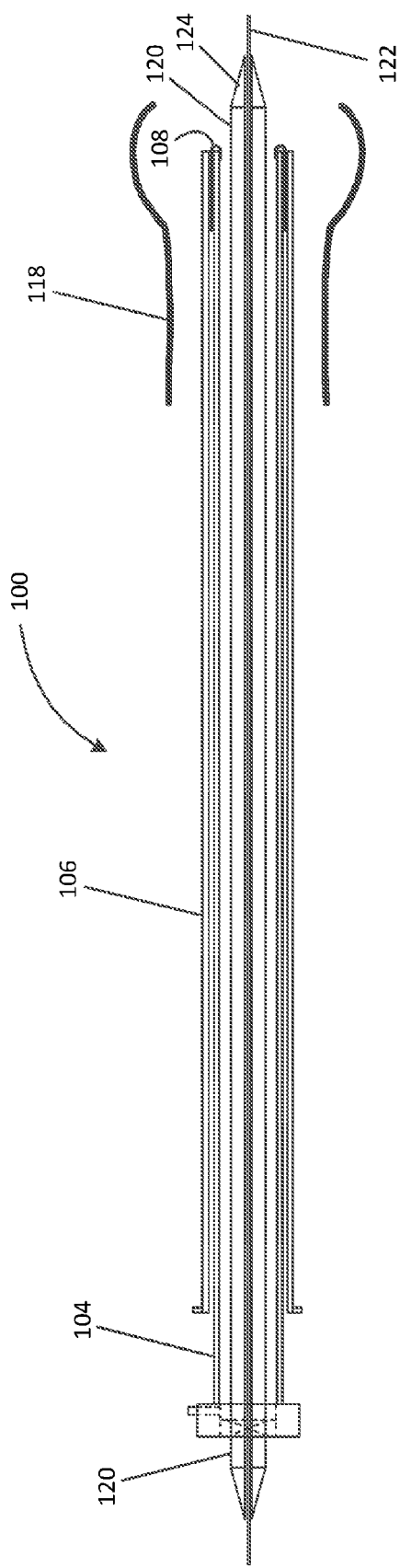
FIG. 2 illustrates the embolic material blocking catheter in the insertion configuration of FIG. 1 positioned in an aorta and an introducer for guiding insertion of the embolic material blocking catheter, in accordance with many embodiments.

FIG. 2 illustrates the embolic material blocking catheter 100 in the insertion configuration and positioned in an aorta 118 and an introducer 120 for guiding insertion of the embolic material blocking catheter 100 to a suitable position for deployment of the embolic material blocking element 108 downstream of a treatment site. In the illustrated embodiment, the introducer 120 is configured to be advanced along a guide wire 122, which is advanced along the insertion route for the embolic material blocking catheter 100 and used to guide the insertion of the introducer 120. The introducer 120 is then used to guide the insertion of the embolic material blocking catheter 100 to a suitable location downstream of the treatment site. In the illustrated embodiment, the introducer 120 has a tapered distal end portion 124 shaped to ease advancement of the introducer 120 along the guide wire 122 and inhibit trauma to patient tissue during advancement of the introducer 120 along the guide wire 122.

The proximal ends of the guide wire 122 and the introducer 120 are inserted into the lumen 112 and the embolic material blocking catheter 100 is advanced over the introducer 120 to position the distal end of the catheter 100 at a suitable location upstream of the treatment site. The introducer 120 can be retracted to remove the introducer 120 after the embolic material blocking catheter 100 has been positioned relative to the treatment site.

Figure 3:
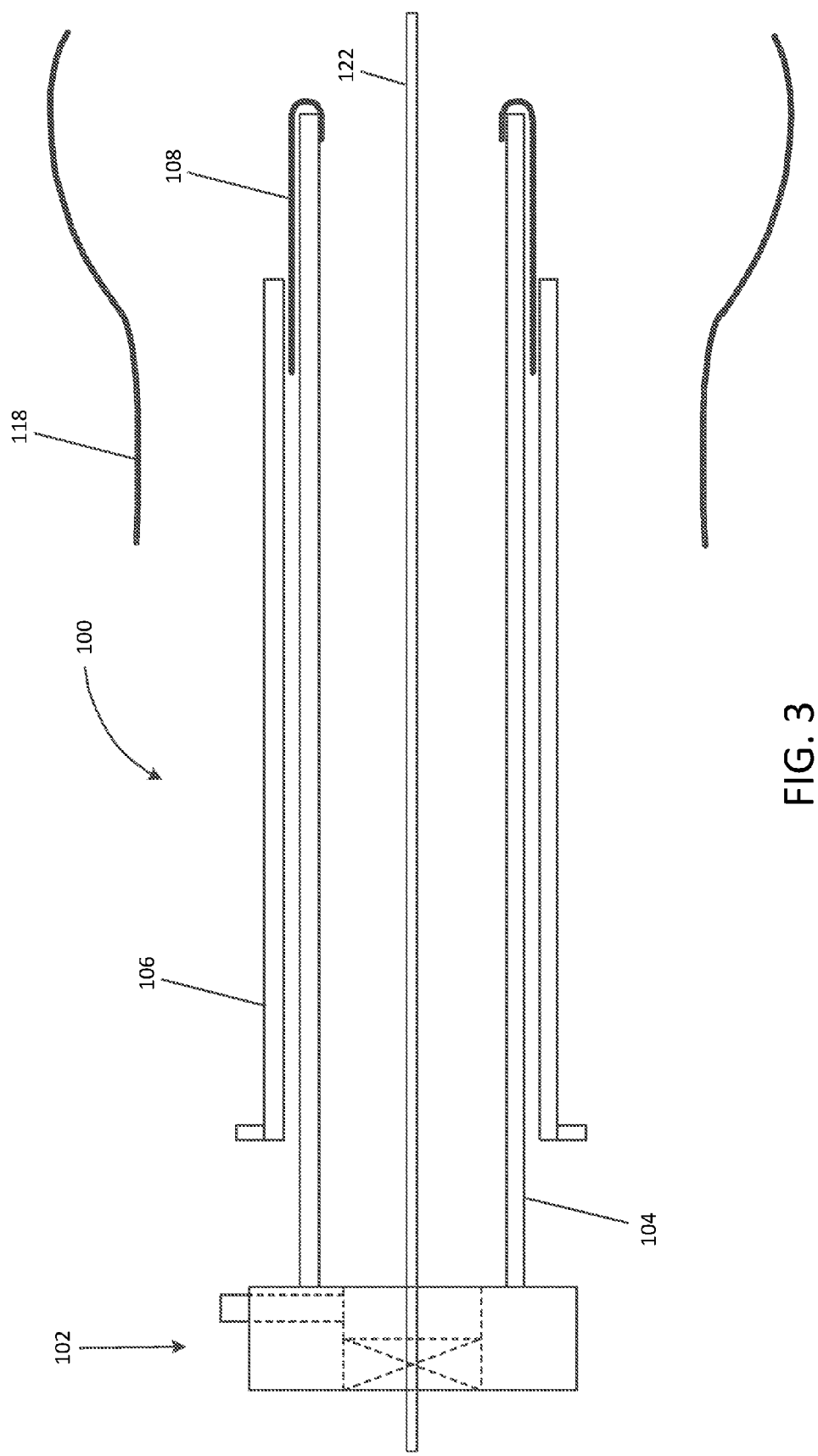
FIG. 3 illustrates the embolic material blocking catheter in the insertion configuration of FIG. 1 positioned in the aorta as in FIG. 2 and following removal of the introducer, in accordance with many embodiments.

FIG. 3 illustrates the embolic material blocking catheter 100 in the insertion configuration and positioned in the aorta 118 and following removal of the introducer 120. In the illustrated configuration, the retention sleeve 106 is shown in a partially retracted position in which the embolic material blocking element 108 remains partially covered by the retention sleeve 106. Further proximal retraction of the retention sleeve 106 results in deployment of the embolic material blocking element 108 to the intermediate deployment configuration illustrated in FIG. 4.

Figure 4:
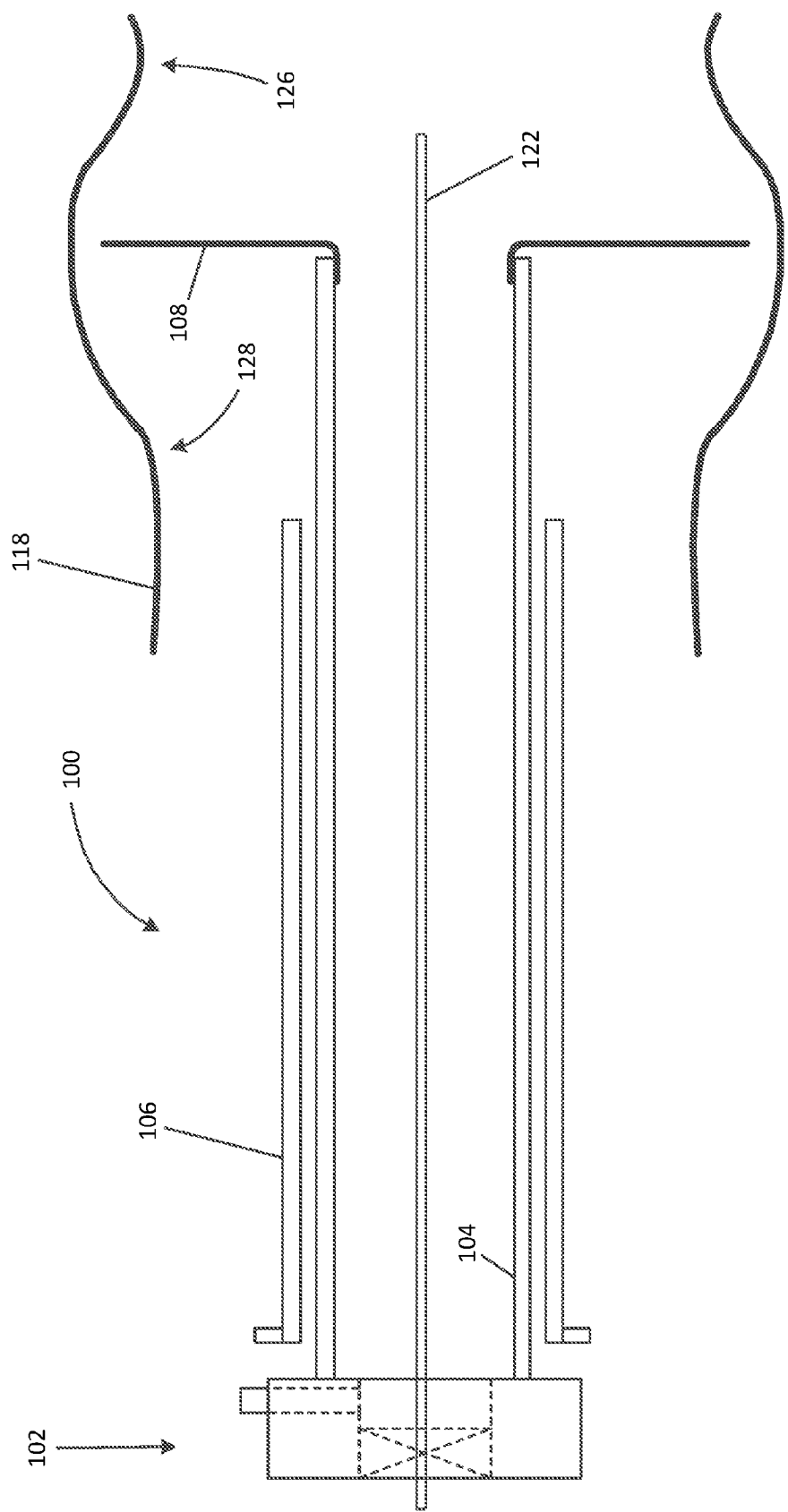
FIG. 4 illustrates the embolic material blocking catheter of FIG. 1 with a retention sheath in a retracted position and an embolic material blocking element deployed to an intermediate deployment configuration between the patient's native aortic valve and the sinotubular junction as a result of proximal retraction of the retention sheath, in accordance with many embodiments.

FIG. 4 shows the embolic material blocking catheter 100 with the embolic material blocking element 108 in the intermediate deployment configuration within the patient's aorta 118 between the native aortic valve 126 and the sinotubular junction 128. The intermediate deployment configuration and position of the embolic material blocking element 108 illustrated in FIG. 4 is accomplished by advancing the distal portion of the embolic material blocking catheter 100 along the patient's aorta 118 to position the embolic material blocking element 108 between the patient's native aortic valve 126 and the sinotubular junction 128. The retention sheath 106 is then retracted proximally relative to the main tube 104 to release the embolic material blocking element 108 thereby allowing the embolic material blocking element 108 to expand into the configuration shown in FIG. 4. In many embodiments, the embolic material blocking element 108 includes a self-expanding frame that supports a filter membrane for filtering embolic material from blood flowing in the aorta 118. The embolic material blocking element 108 can include any suitable membrane, including any suitable filtering or non-filtering membrane.

Figure 5:
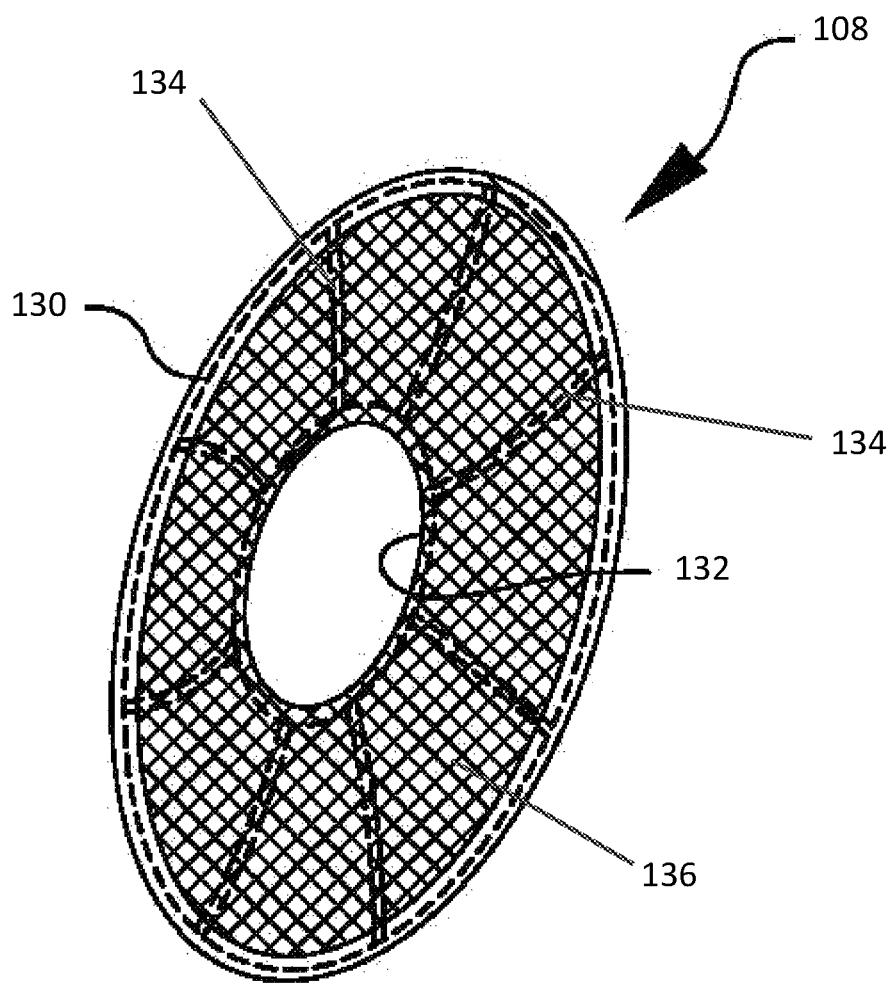
FIG. 5 illustrates an embodiment of the embolic material blocking element in the intermediate deployment configuration of FIG. 4.

In many embodiments, a two-stage process is used to deploy the embolic material blocking element 108. In the first stage, the embolic material blocking element 108 is reconfigured from an initial collapsed configuration to an intermediate deployment configuration illustrated in FIG. 5. In the illustrated embodiment, the embolic material blocking element 108 has a substantially-flat disk shape when in the intermediate deployment configuration. An outer circumferential edge member 130 of the embolic material blocking element 108 is sized to be interfaced with an inner surface of the aorta 118 downstream of the sinotubular junction 128. An inner circumferential edge member 132 is coupled with the main tube 104 of the embolic material blocking catheter 100. With the outer circumferential edge member 130 interfaced with the inner surface of the aorta 118, the main tube 104 is retracted proximally by a suitable distance to reconfigure the embolic material blocking element 108 from the intermediate deployment configuration illustrated in FIG. 5 to the fully deployed configuration illustrated in FIG. 6.

In many embodiments, the embolic material blocking element 108 includes a self-expanding frame structure with shape-memory material frame elements (e.g., nitinol struts 134 and the circumferential edge members 130, 132) and a membrane 136 supported by the shape-memory material frame elements 130, 132, 134. Any suitable membrane material can be used to form the membrane 136, including any suitable permeable or non-permeable materials. In many embodiments, the membrane 136 is configured to filter embolic material from blood flowing through the membrane 136 and along the aorta 118.

Figure 6:
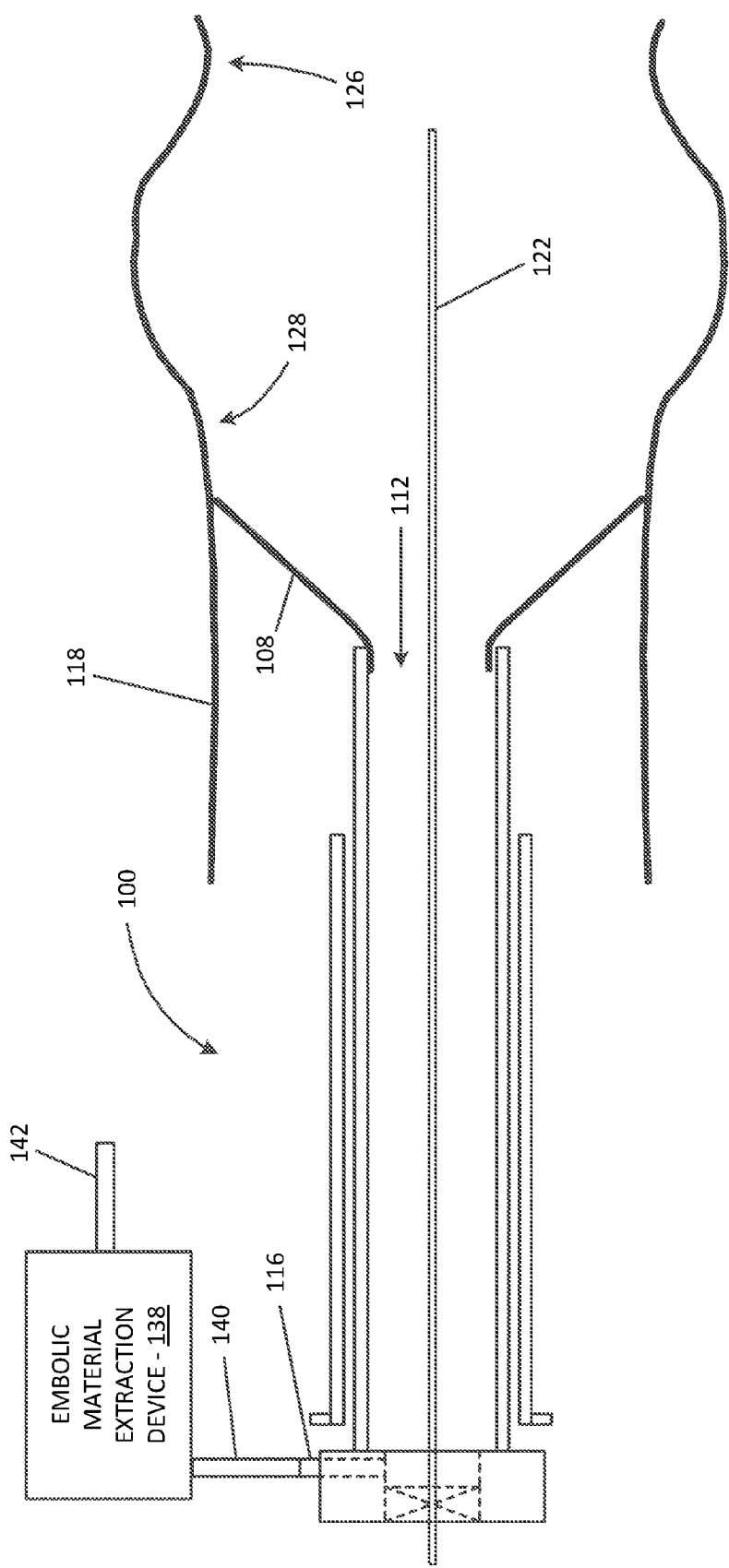
FIG. 6 illustrates the embolic material blocking catheter of FIG. 1 with the deployable embolic material blocking element in a fully deployed configuration and coupled with an embolic material extraction device, in accordance with many embodiments.
Figure 7:
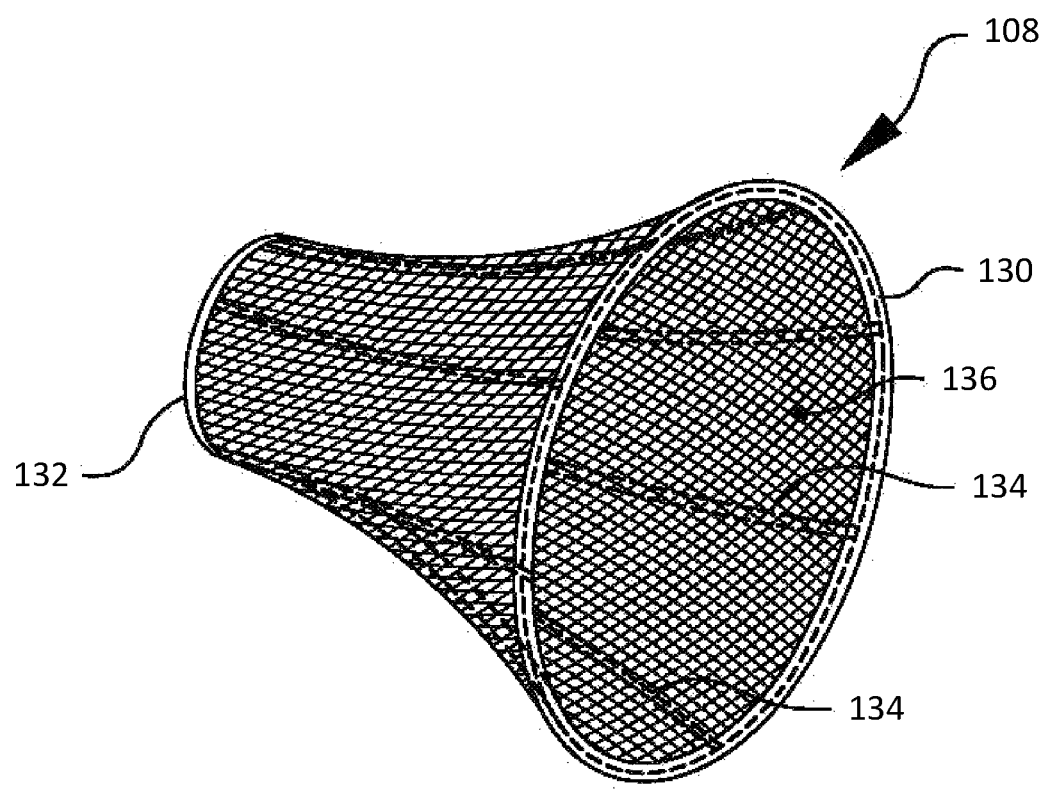
FIG. 7 illustrates an embodiment of the embolic material blocking element in the fully deployed configuration of FIG. 6, in accordance with many embodiments.

FIG. 6 shows the embolic material blocking catheter 100 with the embolic material blocking element 108 fully deployed. The deployed configuration and position of the embolic material blocking element 108 illustrated in FIG. 6 is accomplished by proximally retracting the embolic material blocking catheter 100 to deform the embolic material blocking element 108 from the substantially disk-shaped configuration illustrated in FIG. 4 into a substantially cone-shaped configuration such as illustrated in FIG. 6. An inner circumferential edge of the embolic material blocking element 108 is attached to the main tube 104 near or at the end of the main tube 104. The embolic material blocking element 108 can be sized to have a deployed outer diameter suitable for deployment in the aorta 118 between the native aortic valve 126 and the sinotubular junction 128 and slightly greater than an applicable inner diameter of the aorta 118 downstream of the sinotubular junction 128. As a result, the outer circumferential edge of the embolic material blocking element 108 is restrained from moving proximally by the inner surface of the aorta 188 downstream of the sinotubular junction 128 so that relative proximal movement of the main tube 104 deforms the embolic material blocking element 108 into the substantially cone-shaped configuration illustrated in FIG. 6 and FIG. 7. The cone-shaped membrane of the embolic material blocking element 108 serves to guide captured embolic material inward toward the lumen 112 of the embolic material blocking catheter 100.

In the embodiment shown in FIG. 6, an embolic material extraction device 138 is coupled with the embolic material extraction port 116. The embolic material extraction device 138 includes an inlet 140 and an optional outlet 142. The embolic material extraction device 138 is operable to receive a flow of embolic material intercepted by the embolic material blocking element 108 and blood from the patient mixed with the embolic material. The embolic material extraction device 138 can have any suitable configuration for receiving the mixed flow of embolic material and blood. For example, the embolic material extraction device 138 can be or include a syringe for drawing the mixture of embolic material and blood from the lumen 112. As another example, the embolic material extraction device 138 can include a mechanism to control the internal pressurization within a collection volume within the embolic material extraction device 138 to a suitable pressure less than the blood pressure within the aorta 118 so as to regulate the rate of flow into the collection volume to a suitable rate for removing embolic material intercepted by the embolic material blocking element 108. As another example, the embolic material extraction device 138 can include a pump sized or controllable to transfer the mixture of blood and embolic material from the lumen 112 at a suitable rate. The embolic material extraction device 138 can be configured to separate the blood from the embolic material and output the blood via the outlet 142. The blood output from the outlet 142 can be recirculated back into the patient, such as into a suitable vein of the patient. Alternatively, the mixture of blood and embolic material can be output from the outlet 142 for subsequent separation via a suitable device and the separated blood can be reintroduced back into the patient.

Figure 8:
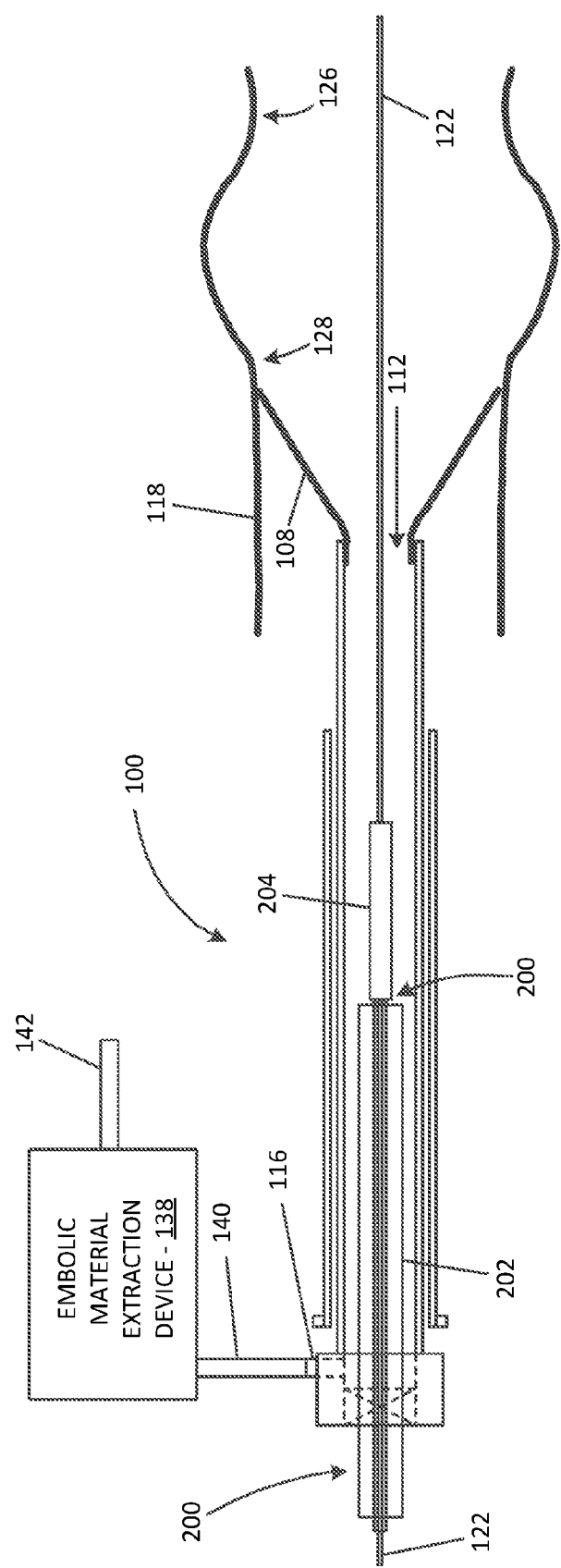
FIG. 8 illustrates a distal portion of a treatment catheter being advanced distally through a lumen of the embolic material blocking catheter of FIG. 1 towards a treatment site upstream of the embolic material blocking element in the fully deployed configuration, in accordance with many embodiments.

FIG. 8 illustrates a treatment catheter 200 being advanced distally along the guide wire 122 through the lumen 112 of the embolic material blocking catheter 100 towards a treatment site (the native aortic valve 126 in FIG. 8) upstream of the embolic material blocking element 108 in the fully deployed configuration, in accordance with many embodiments. In the illustrated embodiment, the treatment catheter 200 includes an elongated body 202 and a treatment member 204 supported via the elongated body 202 at or near the distal end of the treatment catheter 200. The treatment catheter 200 is advanced along the guide wire 122 from a proximal end of the guide wire 122, through the insertion port 114 of the embolic material blocking catheter 100, and through the lumen 112 of the embolic material blocking catheter 100. In many embodiments, the insertion port 114 sealingly interfaces with the treatment catheter 200 to inhibit leakage of blood and/or blood and embolic material from the lumen 112.

The treatment member 204 can be any suitable member operable to administer a treatment at a treatment site upstream of the embolic material blocking element 108 in the fully deployed configuration. For example, in the illustrated embodiment, the treatment member 204 is a balloon that is controllably inflatable to administer balloon angioplasty. Other suitable treatment members 204 include, but are not limited to, balloon for balloon valvuloplasty, covered stents or endografts for repair of aneurysm, dissection or atheroma of the aorta, uncovered stents for relief of obstruction of an artery.

Figure 9:
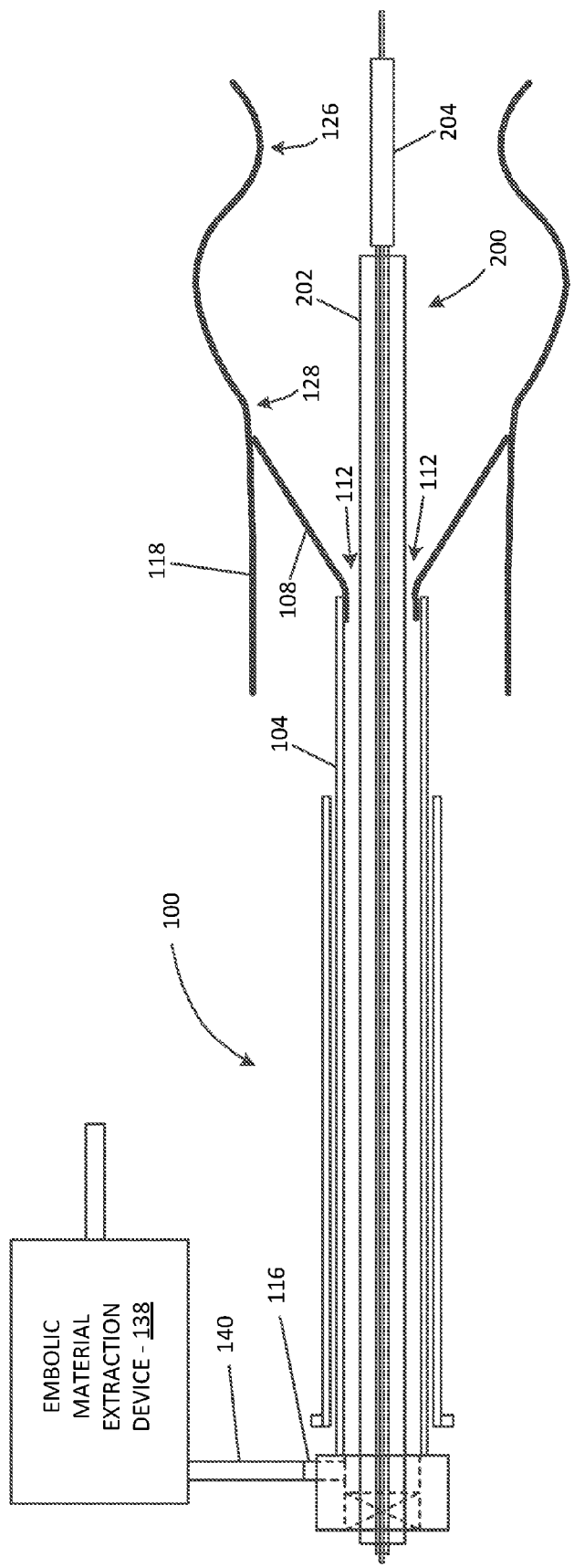
FIG. 9 illustrates the distal portion of the treatment catheter of FIG. 8 positioned at the treatment site after being advance through the lumen of the embolic material blocking catheter of FIG. 1, in accordance with many embodiments.

FIG. 9 illustrates the treatment member 204 of the treatment catheter 200 positioned at the native aortic valve 126 after being advance through the lumen 112 of the embolic material blocking catheter 100. In the illustrated embodiment, the elongated body 202 of the treatment catheter 200 has an outer diameter that is less than the inner diameter of the main tube 104 by a suitable amount so that annular gap of sufficient size exists for conveying a mixture of blood and embolic material at a suitable rate to the embolic material extraction port 116 for output to the embolic material extraction device 138.

Figure 10:
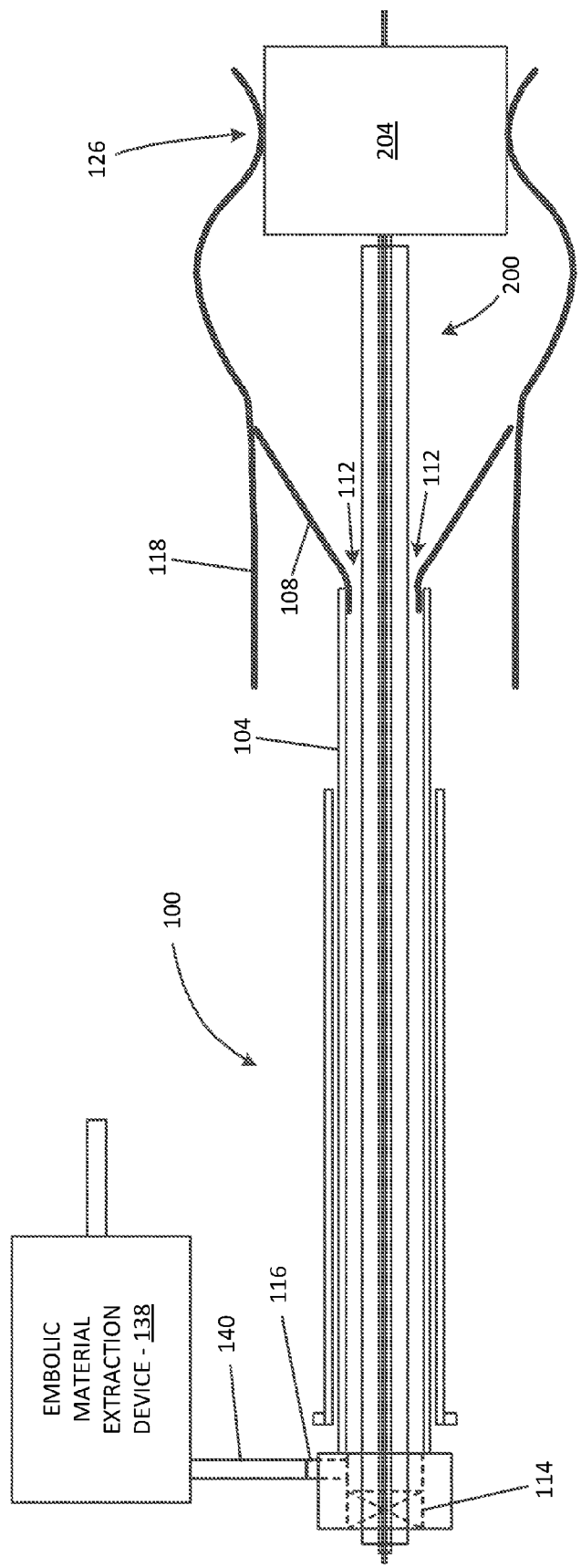
FIG. 10 illustrates treating the treatment site of FIG. 9 via expansion of an expandable member of the treatment catheter, in accordance with many embodiments.

FIG. 10 illustrates application of balloon angioplasty to the native aortic valve 126 via expansion of the treatment member 204 (e.g., expansion of an inflatable balloon). During the application of the balloon angioplasty to the native aortic valve 126, embolic material released into the blood flow along the aorta 118 is captured by the embolic material blocking element 108 and thereby blocked from traveling downstream along the aorta 118 beyond the embolic material blocking element 108. In the illustrated embodiment, the embolic material blocked by the embolic material blocking element 108 is guided to the lumen 112, transported along the lumen 112 in the annular space between the treatment catheter 200 and the inner surface of the main tube 104 of the embolic material blocking catheter 100, and output to the embolic material extraction device 138 through the embolic material extraction port 116. Subsequent to the application of balloon angioplasty to the native aortic valve 126 via expansion of the treatment member 204, the treatment member 204 can be deflated and the treatment catheter 200 removed via proximal retraction along the guide wire 122 and removal from the lumen 112 through the insertion port 114.

Figure 11:
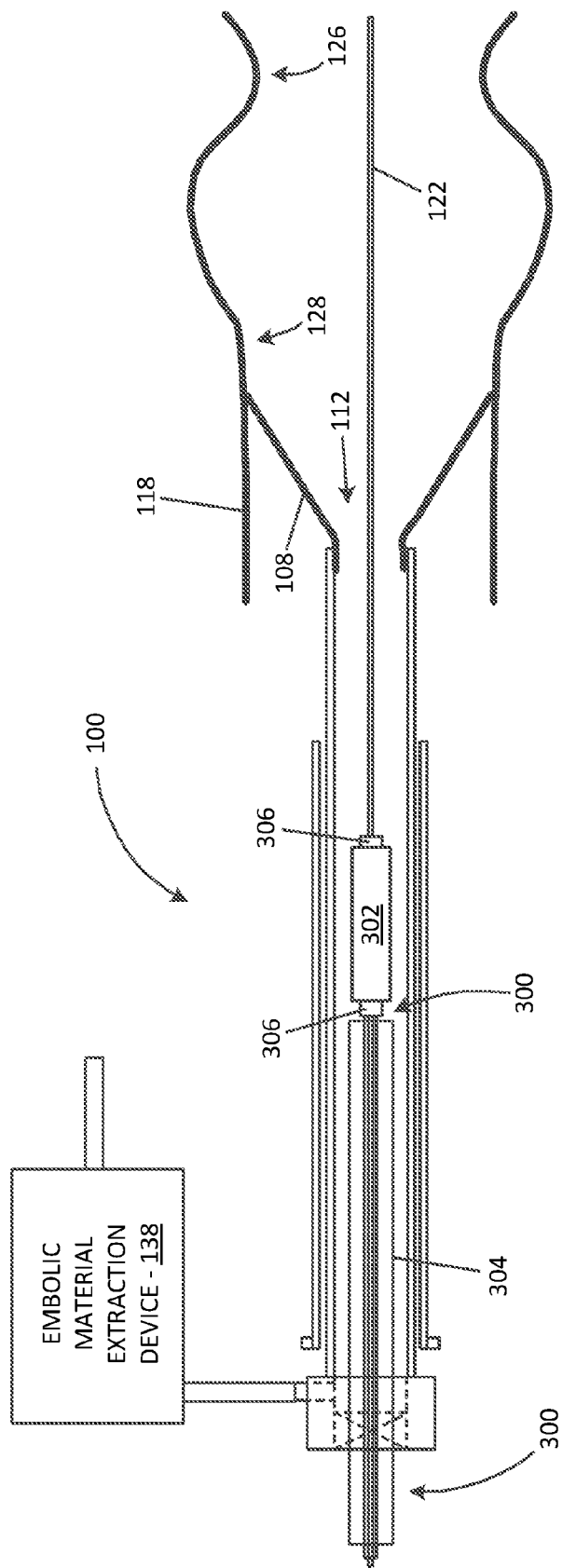
FIG. 11 illustrates a distal portion of a prosthetic valve delivery catheter being advanced distally through the lumen of the embolic material blocking catheter of FIG. 1 towards an implantation site for the prosthetic valve upstream of the embolic material blocking element in the fully deployed configuration, in accordance with many embodiments.

FIG. 11 illustrates a prosthetic valve delivery catheter 300 being advanced distally through the lumen 112 of the embolic material blocking catheter 100 towards an implantation site for a prosthetic valve 302 upstream of the embolic material blocking element 108 in the fully deployed configuration, in accordance with many embodiments. In the illustrated embodiment, the prosthetic valve deliver catheter 300 includes an elongated body 304 and an expandable member 306 (e.g., an inflatable balloon) supported via the elongated body 304 at or near the distal end of the prosthetic valve delivery catheter 300. The prosthetic valve delivery catheter 300 is advanced along the guide wire 122 from a proximal end of the guide wire 122, through the insertion port 114 of the embolic material blocking catheter 100, and through the lumen 112 of the embolic material blocking catheter 100. In many embodiments, the insertion port 114 sealingly interfaces with the prosthetic valve delivery catheter 300 to inhibit leakage of blood and/or blood and embolic material from the lumen 112.

Figure 12:
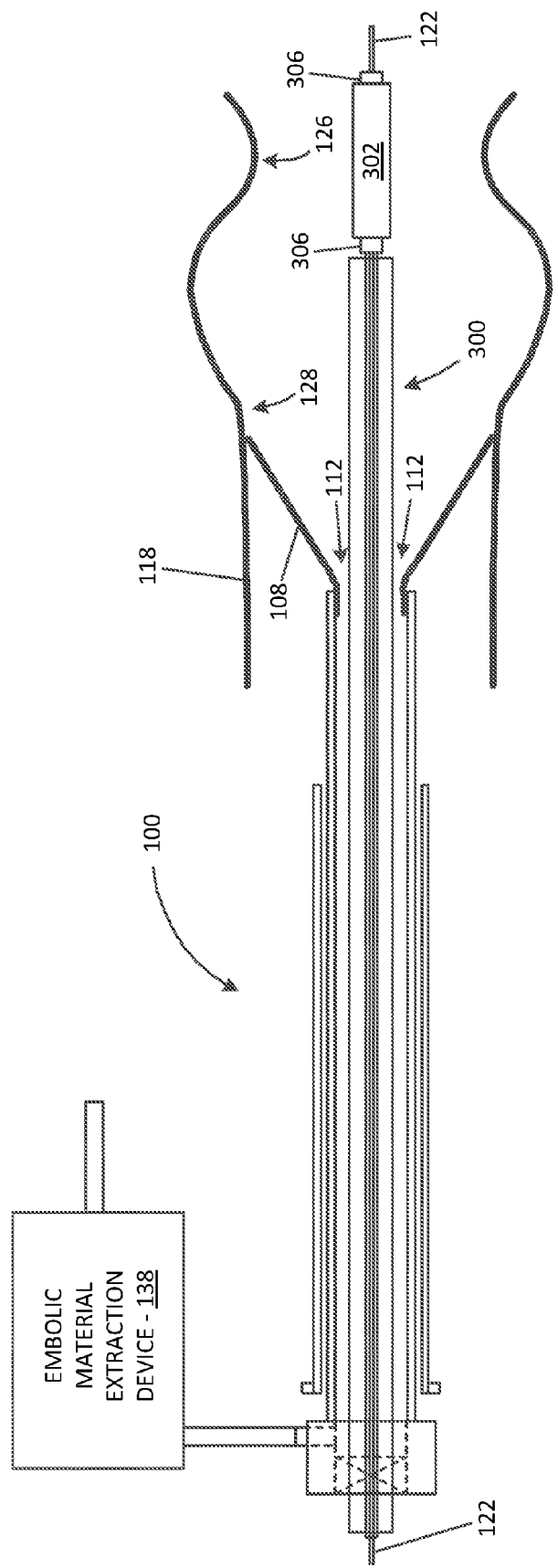
FIG. 12 illustrates the distal portion of the prosthetic valve delivery catheter of FIG. 11 positioned at the implantation site for the prosthetic valve after being advance through the lumen of the embolic material blocking catheter of FIG. 1, in accordance with many embodiments.

FIG. 12 illustrates the expandable member 306 (and the prosthetic valve 302 mounted to the expandable member 306 in a collapsed configuration) positioned for implantation of the prosthetic valve 302 after being advance along the guide wire 122 and through the lumen 112 of the embolic material blocking catheter 100. With the embolic material blocking element 108 deployed downstream of the patient's native aortic valve 126, the embolic material blocking element 108 is positioned to capture embolic material released during deployment of the prosthetic aortic valve 302.

Figure 13:
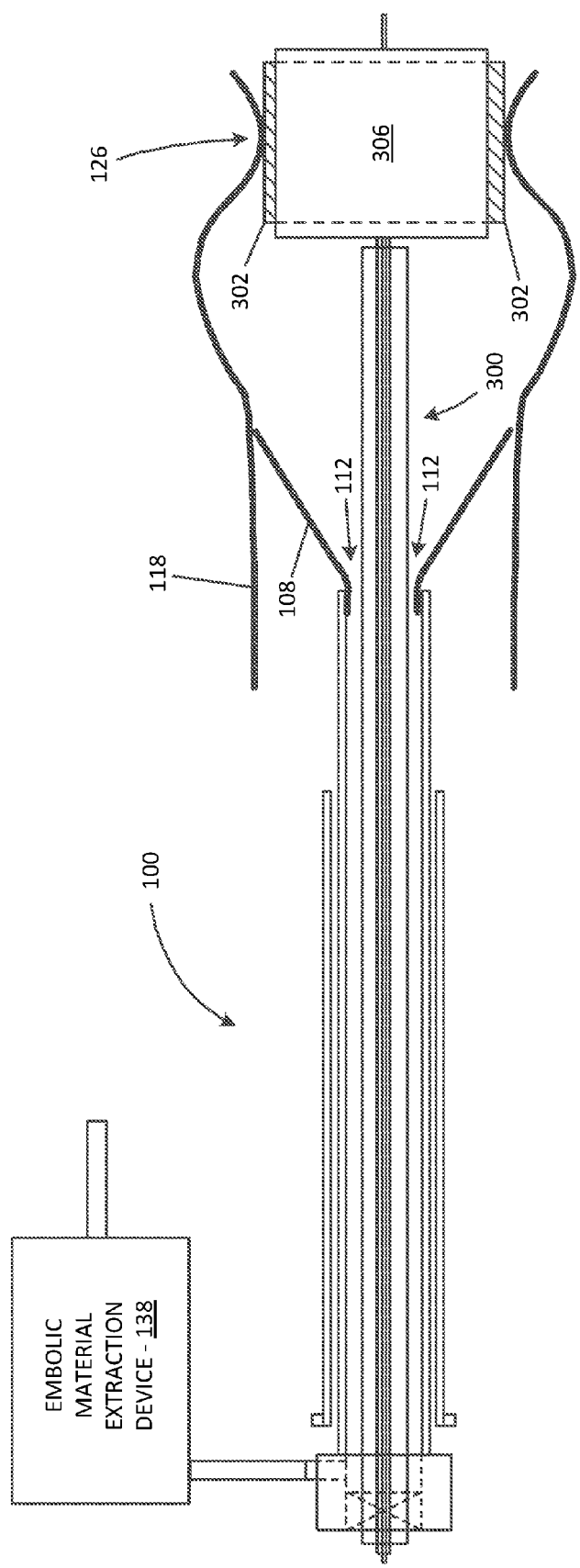
FIG. 13 illustrates deployment of the prosthetic valve at the implantation site via expansion of an expandable member of the prosthetic valve delivery catheter of FIG. 11, in accordance with many embodiments.
Figure 14:
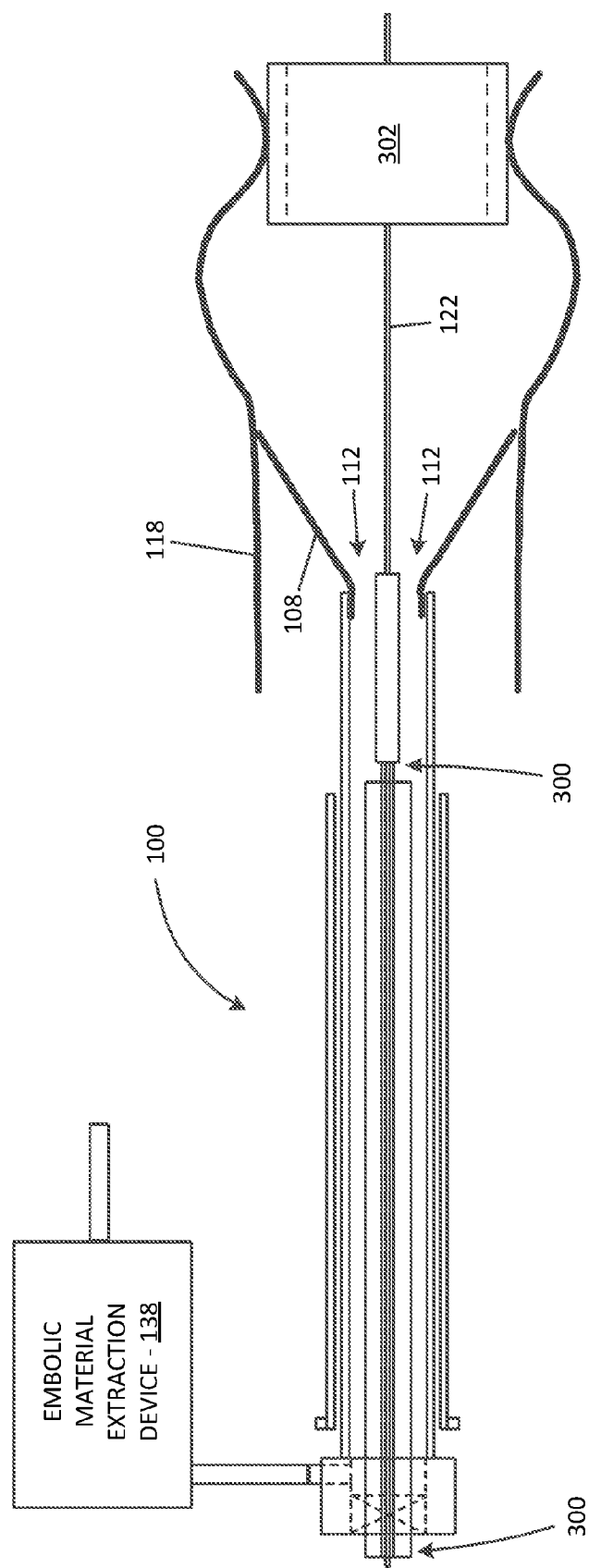
FIG. 14 illustrates the distal portion of the prosthetic valve delivery catheter of FIG. 11 being retracted distally through the lumen of the embolic material blocking catheter of FIG. 1 subsequent to implantation of the prosthetic valve upstream of the embolic material blocking element in the fully deployed configuration, in accordance with many embodiments.

FIG. 13 illustrates deployment of the prosthetic valve 302 at the implantation site via expansion of the expandable member 306. The expansion of the expandable member 306 expands the prosthetic aortic valve 302 into its deployed configuration covering the native aortic valve 126. The expandable member 306 can be expanded during rapid pacing of the patient's heart. Embolic material released during deployment of the prosthetic aortic valve 302 is captured by the embolic material blocking element 108. In the illustrated configuration, the embolic material extraction device 138 is fluidly coupled with the embolic material extraction port 116 and can be operated to remove embolic material gathered by the embolic material blocking element 108 from the patient. FIG. 14 illustrates retraction of the prosthetic valve delivery catheter 300 along the guide wire 122 through the lumen 112 of the embolic material blocking catheter 100 subsequent to implantation of the prosthetic valve 302 upstream of the embolic material blocking element 108 in the fully deployed configuration.

Figure 15:
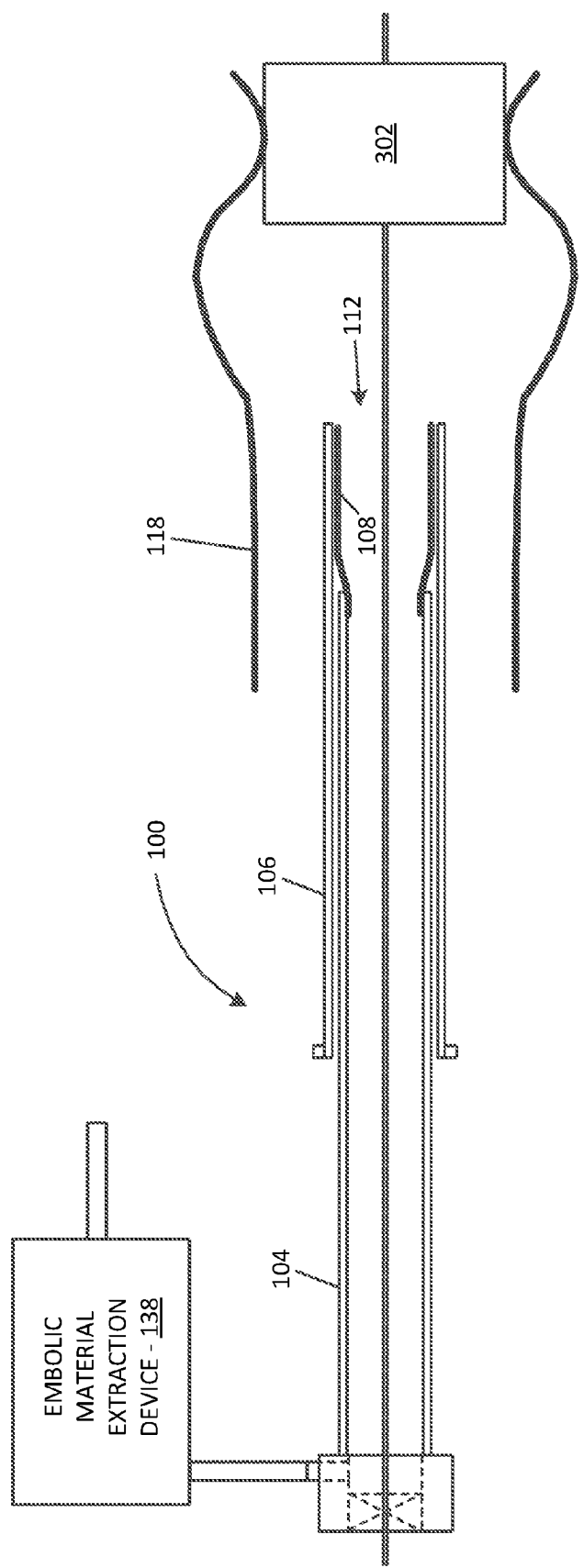
FIG. 15 illustrates the embolic material blocking catheter of FIG. 1 in a configuration in which the embolic material blocking element is in a captured configuration suitable for removal of the embolic material blocking catheter from the patient, in accordance with many embodiments.

FIG. 15 illustrates the embolic material blocking catheter 100 of FIG. 1 in a configuration in which the embolic material blocking element 108 is in a captured configuration suitable for removal of the embolic material blocking catheter 100 from the patient. Following deployment of the prosthetic aortic valve 302, the retention sleeve 106 can be advanced distally along the main tube 104 thereby capturing the embolic material blocking element 108 inside of the retention sleeve 106 prior to withdrawal of the embolic material blocking catheter 100 from the patient. The embolic material extraction device 138 coupled to the embolic material extraction port 116 can be operated during capture of the embolic material blocking element 108 to remove embolic material remaining in the embolic material blocking element 108.

Figure 16:
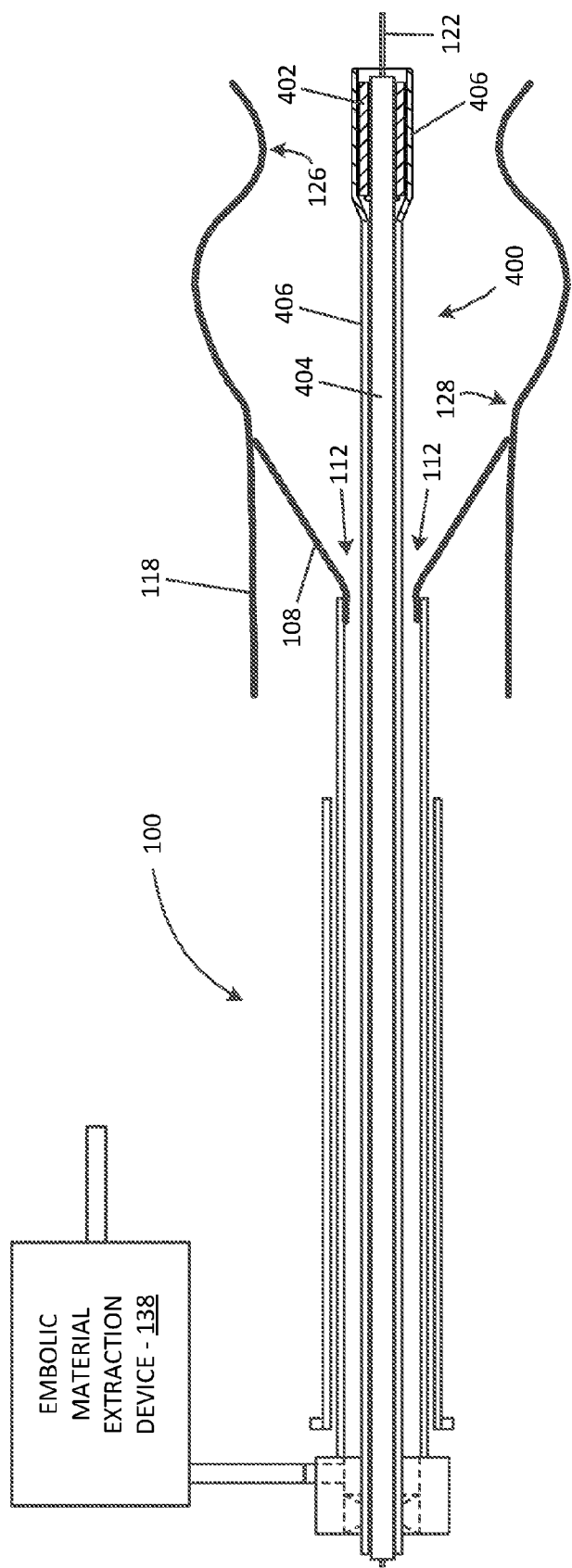
FIG. 16 illustrates the distal portion of a prosthetic valve delivery catheter for a self-expanding prosthetic valve at an implantation site for the self-expanding prosthetic valve after being advance through the lumen of the embolic material blocking catheter of FIG. 1, in accordance with many embodiments.

The embolic material blocking catheter 100 can be used in conjunction with a delivery catheter configured to deploy a self-expanding prosthetic device (e.g., a self-expanding stent, a self-expanding prosthetic aortic valve). For example, FIG. 16 illustrates a self-expanding prosthetic valve delivery catheter 400 configured to deploy a self-expanding prosthetic aortic valve 402 at an implantation site for the self-expanding prosthetic aortic valve 402 after being advance through the lumen 112 of the embolic material blocking catheter 100. The self-expanding prosthetic valve delivery catheter 400 includes an elongated central member 404 and a retention sleeve 406. The self-expanding prosthetic aortic valve 402 is held in a collapsed configuration between the retention sleeve 406 and a distal portion of the central member 404. The self-expanding prosthetic valve delivery catheter 400 is advanced along and over the guide wire 122 and through the lumen 112 to position the self-expanding prosthetic aortic valve 402 in a collapsed configuration at a suitable position relative to the patient's native aortic valve 126 for deployment of the self-expanding prosthetic aortic valve 402.

Figure 17:
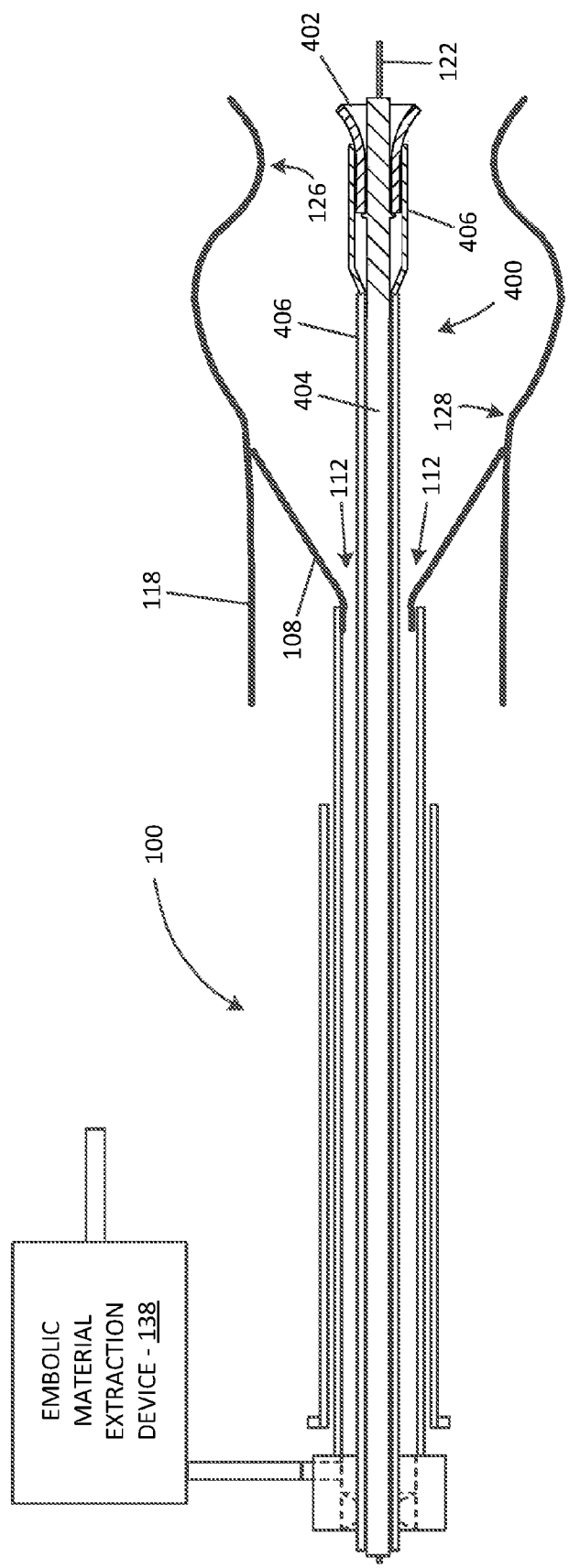
FIG. 17 illustrates a retention sheath of the prosthetic valve delivery catheter of FIG. 16 in an intermediate retracted position during retraction of the retention sheath to deploy the self-expanding prosthetic valve at the implantation site, in accordance with many embodiments.
Figure 18:
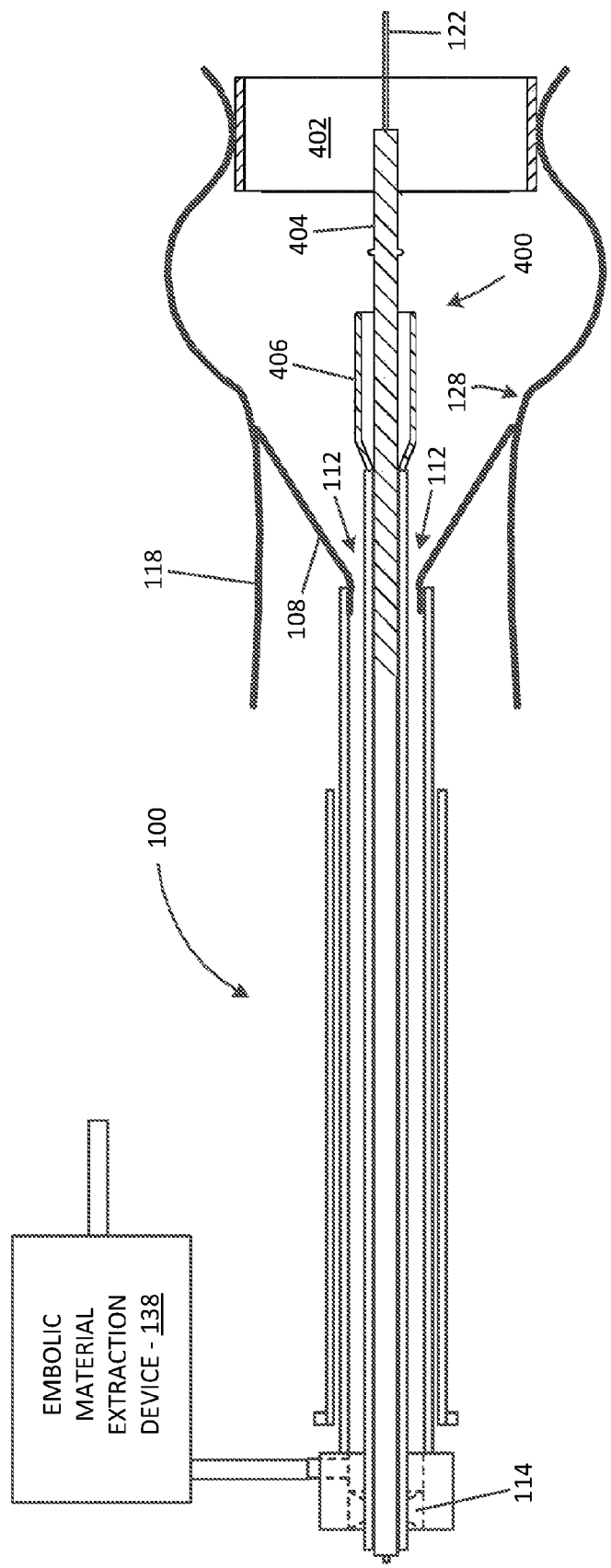
FIG. 18 illustrates the distal portion of the prosthetic valve delivery catheter of FIG. 17 being retracted distally through the lumen of the embolic material blocking catheter of FIG. 1 subsequent to implantation of the self-expanding prosthetic valve upstream of the embolic material blocking element in the fully deployed configuration, in accordance with many embodiments.

Deployment of the self-expanding prosthetic aortic valve 402 is accomplished by retracting the retention sleeve 406 to remove the constraint imposed on the self-expanding prosthetic aortic valve 402 by the retention sleeve 406. FIG. 17 illustrates the retention sheath 406 of the self-expanding prosthetic valve delivery catheter 400 in an intermediate retracted position during retraction of the retention sheath 406 to deploy the self-expanding prosthetic valve 402 at the implantation site. Further retraction of the retention sheath 406 releases the self-expanding prosthetic valve 402, which the self-expands into the configuration illustrated in FIG. 18. Subsequent to deployment of the self-expanding prosthetic valve 402, the self-expanding prosthetic valve delivery catheter 400 can be removed via retraction of the delivery catheter 400 along the guide wire 122 and through the lumen 112 and the insertion port 114 of the embolic material blocking catheter 100. For example, FIG. 18 illustrates the self-expanding prosthetic valve delivery catheter 400 being retracted distally through the lumen 112 of the embolic material blocking catheter 100 subsequent to implantation of the self-expanding prosthetic valve 402 upstream of the embolic material blocking element 108 in the fully deployed configuration.

Figure 19:
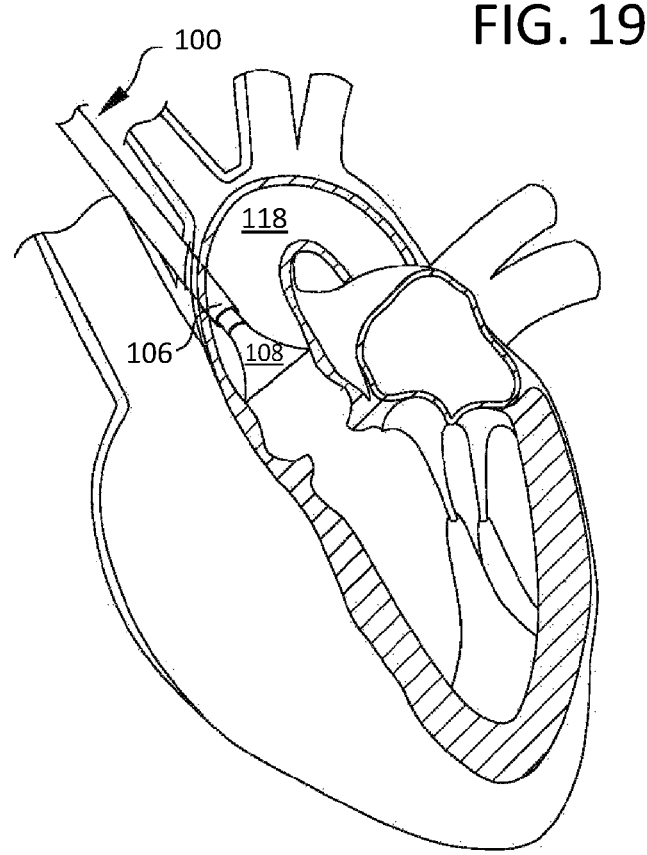
FIG. 19 is a partial cross-sectional view illustrating the embolic material blocking catheter of FIG. 1 with the embolic material blocking element fully deployed in a patient's aorta downstream of an implantation site via a direct trans-aortic (TAo) approach, in accordance with many embodiments.
Figure 20:
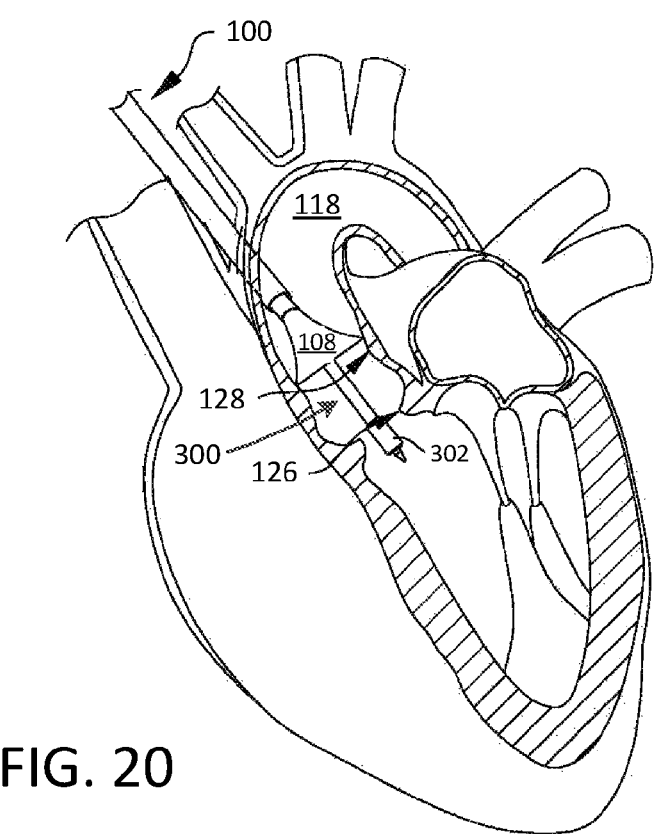
FIG. 20 is a partial cross-sectional view illustrating a prosthetic valve delivery catheter inserted through the embolic material blocking catheter of FIG. 19 to position a prosthetic valve for implantation upstream of the deployed embolic material blocking element, in accordance with many embodiments.
Figure 21:
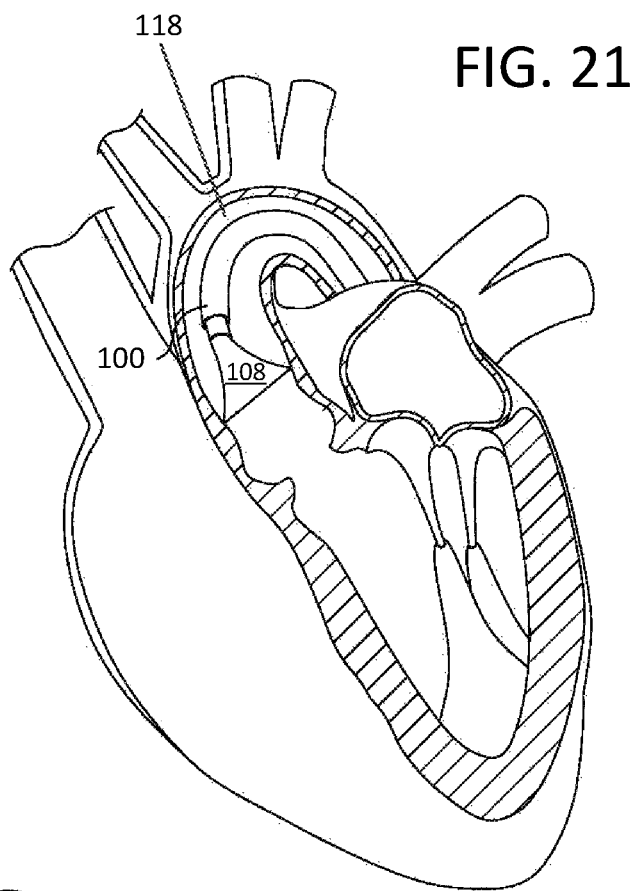
FIG. 21 is a partial cross-sectional view illustrating the embolic material blocking catheter of FIG. 1 with the embolic material blocking element fully deployed in a patient's aorta downstream of an implantation site via a trans-femoral approach, in accordance with many embodiments.
Figure 22:
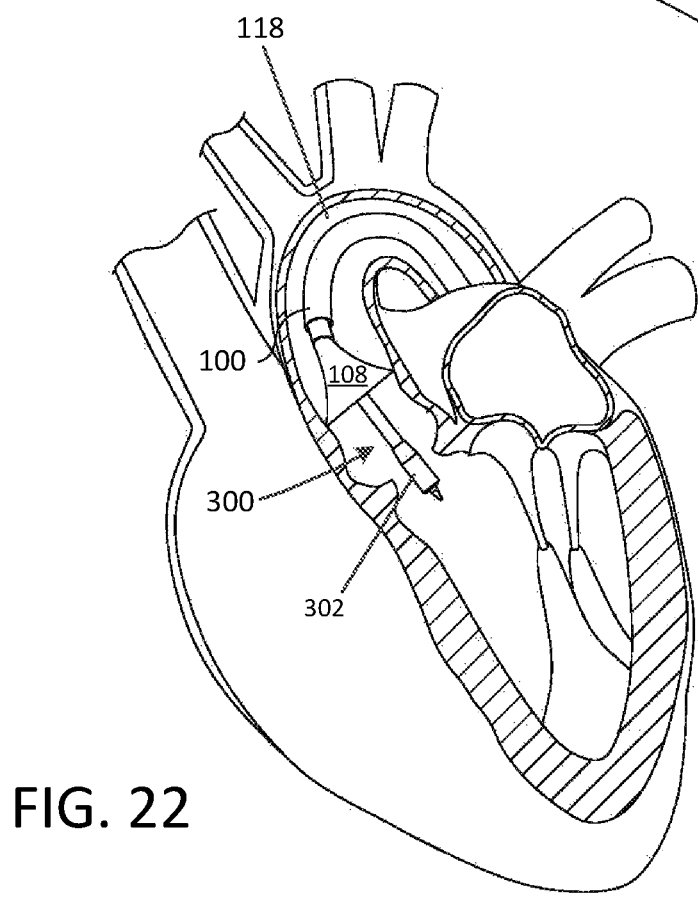
FIG. 22 is a partial cross-sectional view illustrating a prosthetic valve delivery catheter inserted through the embolic material blocking catheter of FIG. 21 to position a prosthetic valve for implantation upstream of the deployed embolic material blocking element, in accordance with many embodiments.

Any suitable insertion route for the embolic material blocking catheter 100 can be used to position the embolic material blocking element 108 (in the fully deployed configuration) downstream of a treatment site so as to capture embolic material released via application of a treatment at the treatment site. For example, FIG. 19 is a partial cross-sectional view illustrating the embolic material blocking catheter 100 positioned with the embolic material blocking element 108 fully deployed in a patient's aorta 118 downstream of an implantation site for a prosthetic aortic valve via a direct trans-aortic (TAo) approach. FIG. 20 is a partial cross-sectional view illustrating a prosthetic valve delivery catheter 300 inserted through the embolic material blocking catheter 100 (inserted via a direct trans-aortic (TAo) route illustrated in FIG. 19) to position a prosthetic valve 302 for implantation upstream of the deployed embolic material blocking element 108. As another example, FIG. 21 is a partial cross-sectional view illustrating the embolic material blocking catheter 100 positioned with the embolic material blocking element 108 fully deployed in a patient's aorta 118 downstream of an implantation site for a prosthetic aortic valve via a trans-femoral approach. FIG. 22 is a partial cross-sectional view illustrating a prosthetic valve delivery catheter 300 inserted through the embolic material blocking catheter 100 (inserted via the trans-femoral route illustrated in FIG. 21) to position a prosthetic valve 302 for implantation upstream of the deployed embolic material blocking element 108.

Figure 23:
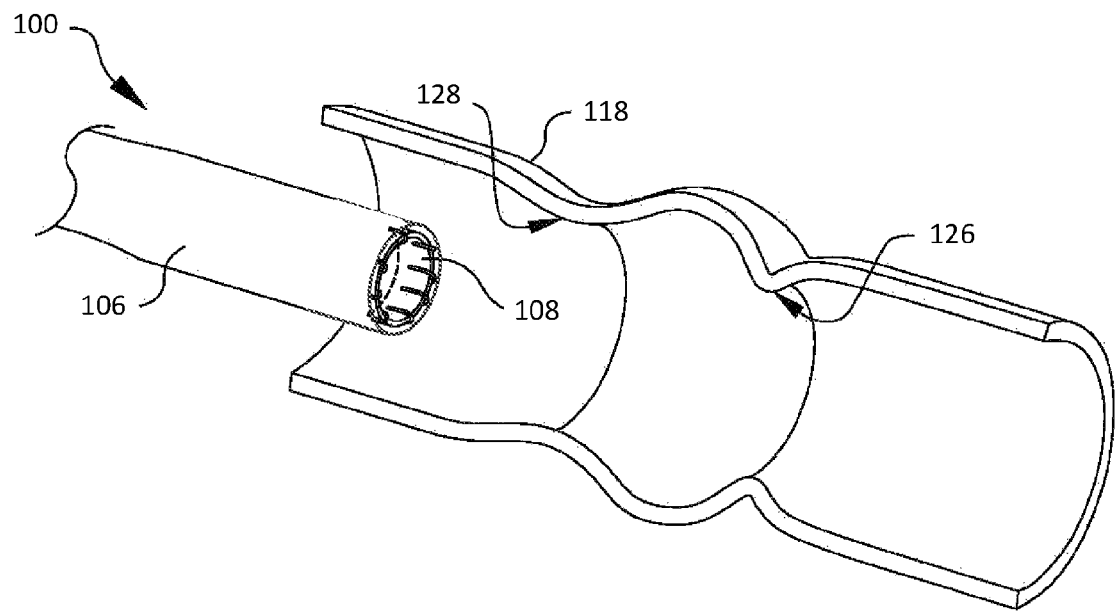
FIG. 23 is a partial cross-sectional view illustrating the distal portion of the embolic material blocking catheter of FIG. 1 being advanced distally towards a left ventricle of a patient's heart prior to deployment of the deployable embolic material blocking element in the patient's aorta, in accordance with many embodiments.
Figure 24:
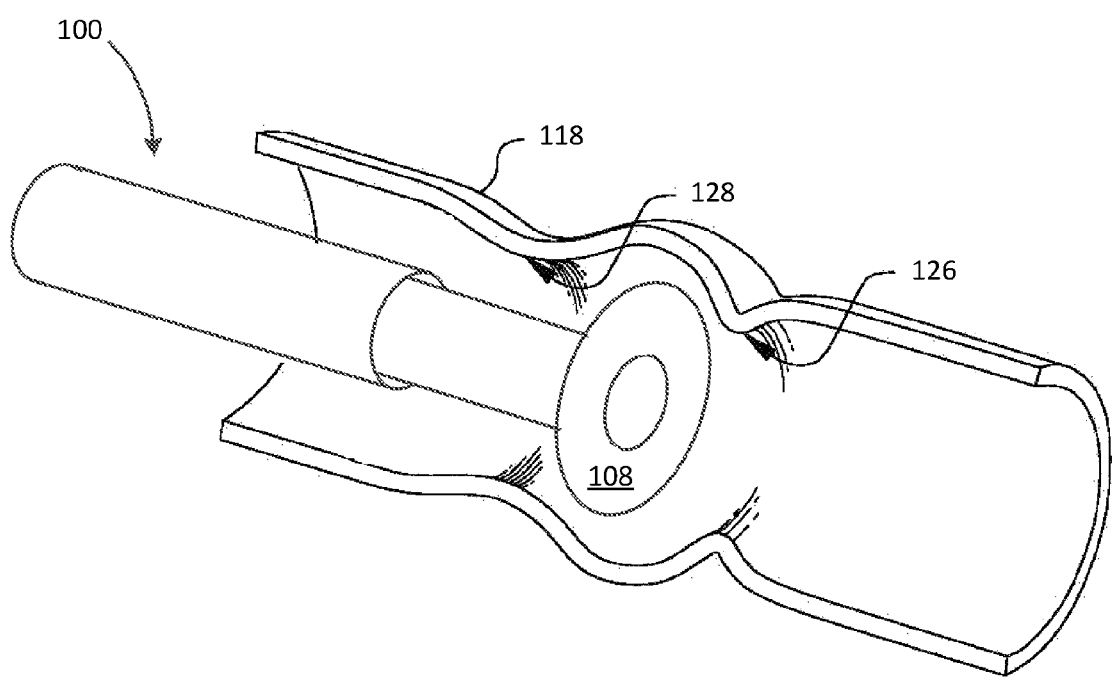
FIG. 24 is a partial cross-sectional view illustrating the distal portion of the embolic material blocking catheter of FIG. 1 with the embolic material blocking element deployed between the patient's native aortic valve and the sinotubular junction to an intermediate deployment configuration, in accordance with many embodiments.
Figure 25:
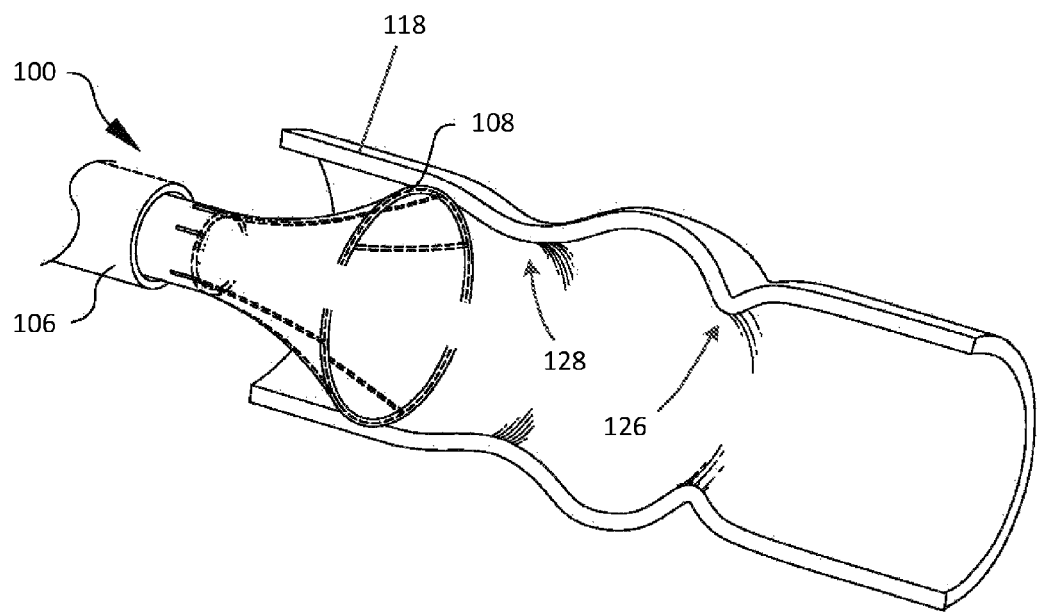
FIG. 25 is a partial cross-sectional view illustrating the distal portion of the embolic material blocking catheter of FIG. 1 with the embolic material blocking element fully deployed, in accordance with many embodiments.
Figure 26:
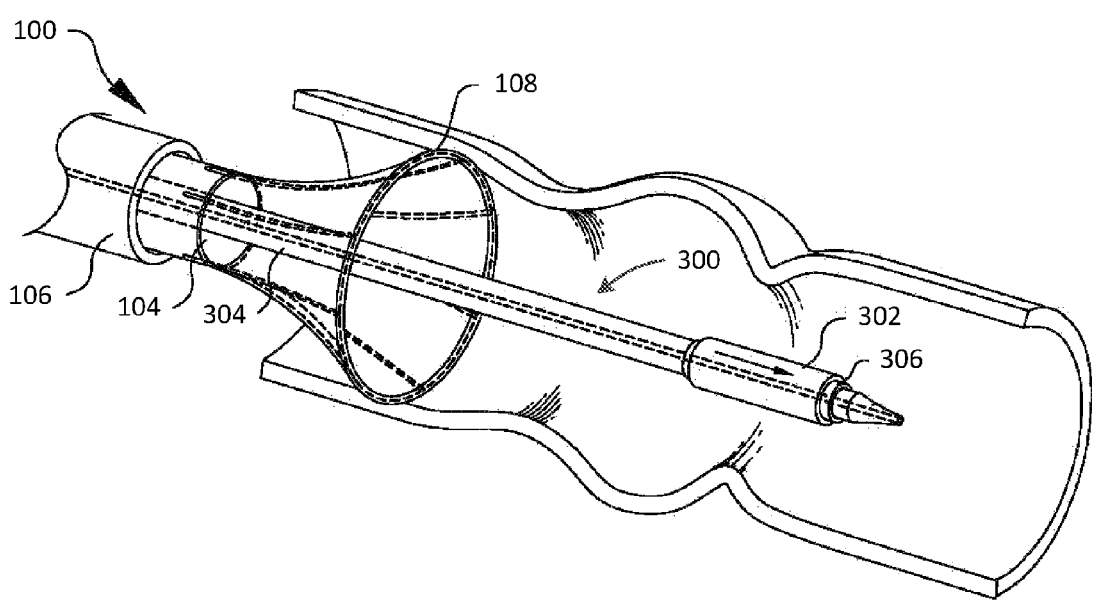
FIG. 26 illustrates the distal portion of a prosthetic valve delivery catheter positioned at an implantation site for the prosthetic valve after being advance through the lumen of the embolic material blocking catheter of FIG. 1, in accordance with many embodiments.
Figure 27:
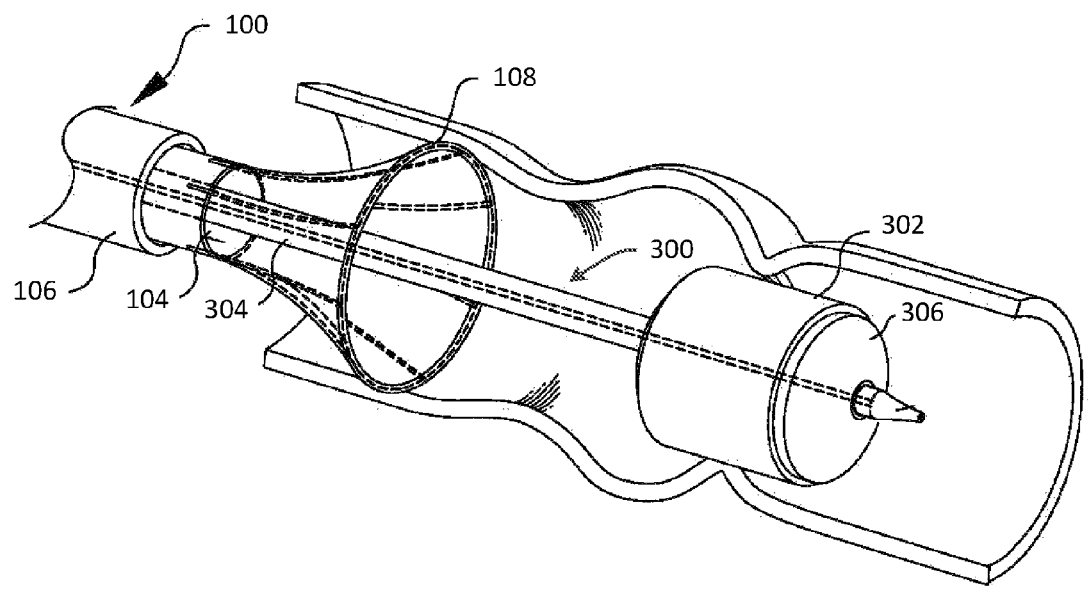
FIG. 27 illustrates deployment of the prosthetic valve at the implantation site via expansion of an expandable member of the prosthetic valve delivery catheter of FIG. 26, in accordance with many embodiments.
Figure 28:
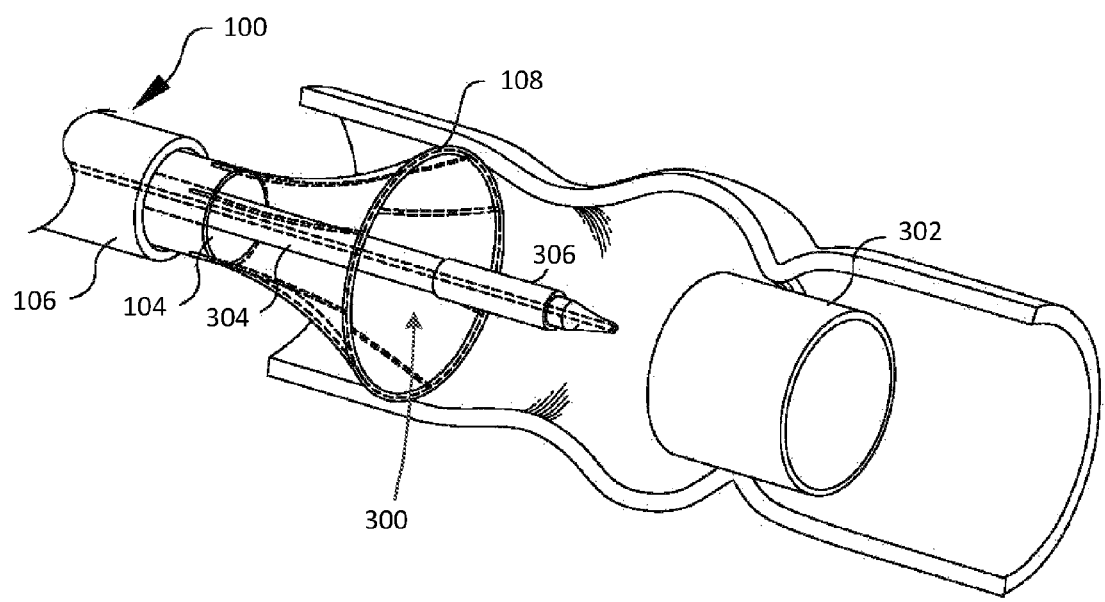
FIG. 28 illustrates the distal portion of the prosthetic valve delivery catheter of FIG. 27 being retracted distally through the lumen of the embolic material blocking catheter of FIG. 1 subsequent to implantation of the prosthetic valve upstream of the embolic material blocking element in the fully deployed configuration, in accordance with many embodiments.
Figure 29:
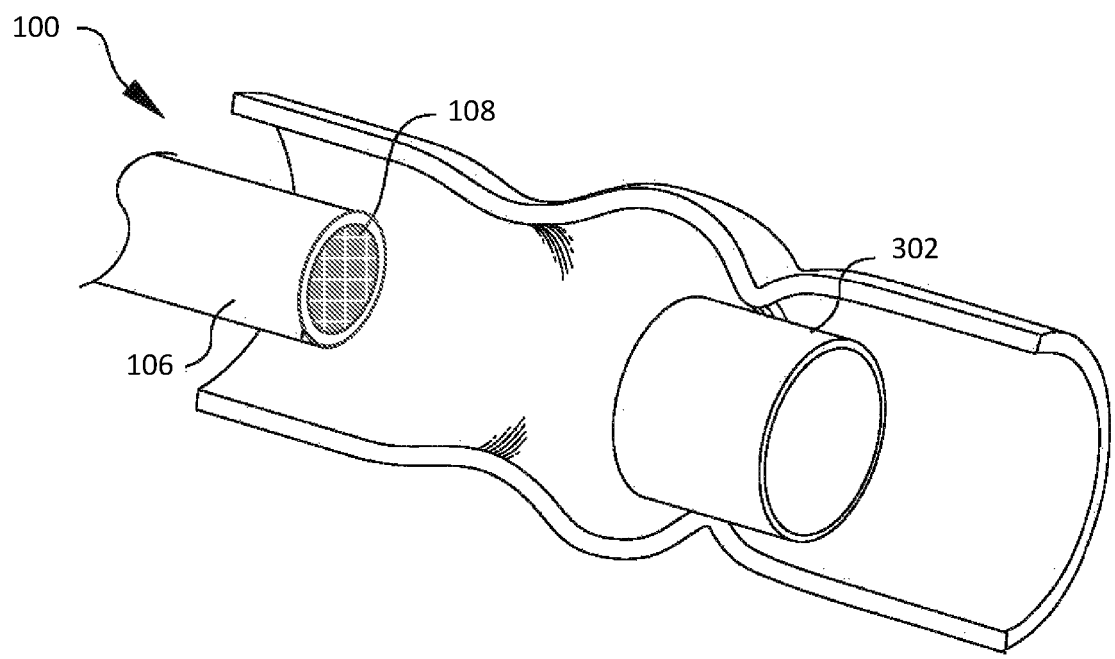
FIG. 29 illustrates the embolic material blocking catheter of FIG. 1 in a configuration in which the embolic material blocking element is in a captured configuration suitable for removal of the embolic material blocking catheter from the patient subsequent to implantation of the prosthetic valve, in accordance with many embodiments.

FIG. 23 through FIG. 29 further illustrate the implantation of a prosthetic aortic valve 302 via the delivery catheter 300 in conjunction with the embolic material blocking catheter 100. FIG. 23 is a partial cross-sectional view illustrating the distal portion of the embolic material blocking catheter 100 being advanced distally towards a left ventricle of a patient's heart prior to deployment of the deployable embolic material blocking element 108 in the patient's aorta, in accordance with many embodiments. FIG. 24 is a partial cross-sectional view illustrating the distal portion of the embolic material blocking catheter 100 with the embolic material blocking element 108 deployed between the patient's native aortic valve 126 and the sinotubular junction 128 to the intermediate deployment configuration. FIG. 25 is a partial cross-sectional view illustrating the distal portion of the embolic material blocking catheter 100 with the embolic material blocking element 108 fully deployed in the aorta 118 downstream of the sinotubular junction 128. FIG. 26 illustrates the distal portion of a prosthetic valve delivery catheter 300 after being inserted through the lumen 112 of the embolic material blocking catheter 100 to position the prosthetic aortic valve 302 for implantation. FIG. 27 illustrates deployment of the prosthetic aortic valve 302 at the implantation site via expansion of the expandable member 306 of the prosthetic valve delivery catheter 300. FIG. 28 illustrates the distal portion of the prosthetic valve delivery catheter 300 being retracted distally through the lumen 112 of the embolic material blocking catheter 100 subsequent to implantation of the prosthetic aortic valve 302. FIG. 29 illustrates the embolic material blocking catheter 100 in a configuration in which the embolic material blocking element 108 has been captured via distal advancement of the retention sleeve 106 and suitable for removal of the embolic material blocking catheter 100 from the patient.

The embolic material blocking catheter 100 can be used by itself to block downstream migration of embolic material through a blood vessel from a treatment site or in conjunction with any suitable treatment catheter deployable through the insertion port 114 and the lumen 112 of the embolic material blocking catheter 100. The embolic material blocking catheter 100 can also be used in any suitable treatment in which embolic material may be released from a treatment site including, but not limited to, balloon angioplasty, balloon valvuloplasty, stent implantation (covered or bare), coronary bypass surgery, and/or prosthetic valve implantation. Furthermore, the embolic material blocking catheter 100 may be deployed by itself while performing transcatheter procedures on other cardiac valve to capture liberated embolic material. For example, the embolic material blocking catheter 100 may be used in catheter based mital valve interventions (e.g., balloon valvuloplasty or replacement) to provide proximal aortic embolic protection to prevent harmful embolization to the systemic or cerebral circulation.

Any suitable treatment catheter can be integrated with the embolic material blocking catheter 100 to form an integrated treatment and embolic material blocking catheter having the combined functionality of the treatment catheter and the embolic material blocking catheter 100. For example, any of the treatment catheters 200, 300, 400 described herein can be integrated with the embolic material blocking catheter 100 to form a corresponding integrated treatment catheter having the combined functionality of the treatment catheter and the embolic material blocking catheter 100.

Figure 30:
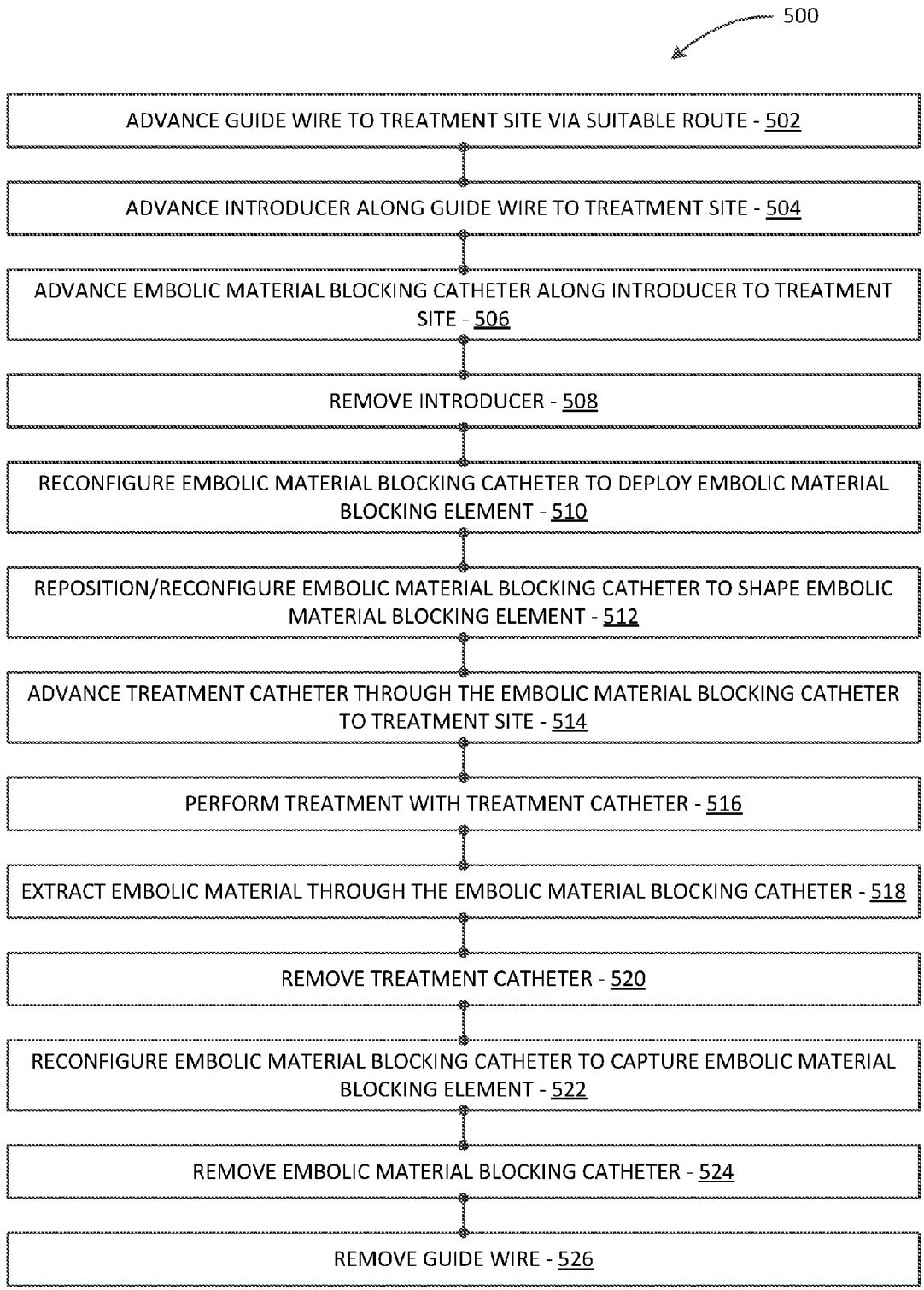
FIG. 30 is a simplified block diagram of acts of a method for performing a treatment at a treatment site within a blood vessel while blocking downstream distribution of embolic material released from the treatment site, in accordance with many embodiments.

FIG. 30 is a simplified block diagram of acts of a method 500 for performing a treatment at a treatment site within a blood vessel while blocking downstream distribution of embolic material released from the treatment site, in accordance with many embodiments. The method 500 can be practiced using any suitable device or devices, including the embolic material blocking catheter 100, the treatment catheter 200, the prosthetic valve delivery catheter 300, and the self-expanding prosthetic valve delivery catheter 400 described herein. While the method 500 is described herein with reference to the catheters 100, 200, 300, 400 described herein, the method 500 can be practiced using any other suitable device or devices. Additionally, the method 500 can be used to perform any suitable treatment, including the treatments indicated herein.

In act 502, a guide wire 122 is advanced to the treatment site via any suitable route. For example, when the treatment site is a patient's native aortic valve 126, the guide wire can be advanced to the patient's native aortic valve via any suitable route including, but not limited to, a trans-femoral route, a direct access trans-aortic (TAo) route, a brachiocephalic route, a carotid route, and an axillary route.

In act 504, an introducer 120 is advanced along the guide wire 122 to the treatment site. In many embodiments, the introducer 120 has a suitable outer diameter with respect to the inner diameter of the lumen 112 of the embolic material blocking catheter 100 to guide advancement of the embolic material blocking catheter over the introducer 120.

In act 506, the embolic material blocking catheter 100 is advanced along the introducer 120 to position the embolic material blocking element 108 for deployment. In many embodiments, the embolic material blocking element 108 is positioned to be deployed upstream of an intended fully deployed location for the embolic material blocking element 108 to accommodate proximal retraction of the catheter 100 used to reconfigure the embolic material blocking element 108 from the intermediate deployment configuration to the fully deployed configuration. Subsequent to the advancement of the embolic material blocking catheter 100 along the introducer 120, the introducer 120 is removed via retraction of the introducer along the guide wire 122 and out through the insertion port 114 of the embolic material blocking catheter 100 (act 508).

In act 510, the embolic material blocking catheter 100 is reconfigured to deploy the embolic filter blocking element 108. The retention sleeve 106 is retracted to release the embolic material blocking element 108, which then expands into the intermediate deployment configuration.

In act 512, the embolic material blocking catheter 100 is retracted away from the treatment site to reconfigure the embolic material blocking element 108 from the intermediate deployment configuration to the fully deployed (e.g., cone-shaped) configuration. The fully deployed configuration of the embolic material blocking element 108 helps to guide embolic material intercepted by the embolic material blocking element 108 to the lumen 112 of the embolic material blocking catheter 100.

In act 514, a treatment catheter (e.g., any one of the treatment catheters 200, 300, 300) is advanced to the treatment site through the insertion port 114 and the lumen 112. The treatment catheter can be configured to perform any suitable treatment at the treatment site and the embolic material blocking catheter 100 can be used to capture embolic material released from the treatment site as a result of the treatment performed.

In act 516, the treatment catheter is used to perform the treatment at the treatment site. Embolic material released from the treatment site as a result of the performance of the treatment is intercepted by the embolic material blocking element 108. In act 518, embolic material intercepted by the embolic material blocking element 108 is conveyed along the lumen 112 of the embolic material blocking catheter 100 and removed via the embolic material extraction port 116.

Subsequent to completion of performance of the treatment at the treatment site, the treatment catheter is removed via retraction through the lumen 112 and the insertion port 114 of the embolic material blocking catheter 100 (act 520). The embolic material blocking catheter 100 is reconfigured via distal advancement of the retention sleeve 106 to capture the embolic material blocking element 108 (act 522). Subsequent to the capture of the embolic material blocking element 108, the embolic material blocking catheter 100 is removed from the patient via proximal retraction (act 524). In act 526, which can occur at any suitable point during the method 500, the guide wire 122 is removed from the patient via proximal retraction (act 526).

The devices and methods described herein are expected to produce substantial benefits in the way of substantially increased safety and efficacy of transcatheter aortic valve replacement (TAVR). The resulting improved TAVR is expected to enable TAVR to be performed on a substantially increased number of patients and improve outcomes and reduce recovery times relative to existing TAVR and SAVR procedures. Specifically, there will be less embolic material conveyed within the circulation system, thereby lowering the incidence of clinical stroke, subclinical stroke, silent cerebral embolization, renal embolization, mesenteric embolization, and peripheral embolization and each of the associated clinical syndromes.

The embolic material blocking catheter 100 is also suitable for use in procedures involving covered or uncovered stenting of arteries for capture and extraction of embolic material that may be liberated during their implantation for the treatment of aneurysms, dissections, stenosis or thrombus. The embolic material blocking catheter 100 is also suitable for prevention of injury resulting from embolic events occurring during balloon aortic valvuloplasty. The embolic material blocking catheter 100 is also suitable for prevention of tissue injury resulting from the performance of mitral balloon valvuloplasty or replacement. In the case of mitral procedures, the embolic protection provided by the embolic material blocking catheter 100 may be separate from a delivery catheter. In this situation there may be a separate transvenous or transapical implantation system of sheaths and catheters for valve delivery and deployment and the embolic material blocking catheter 100 can be deployed in the ascending aorta for capture and elimination of the material liberated from the mitral valve manipulation.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system for implanting a prosthetic aortic valve into a patient having an aorta, the system comprising:
   an embolic material blocking catheter including:
      a handle assembly;
      an elongated element having a proximal portion coupled with the handle assembly, a distal portion, and a lumen extending through the distal portion; and
      an embolic material blocking element connected to the distal portion of the elongated element, the embolic material blocking catheter being reconfigurable from a first configuration in which the embolic material blocking element is in an insertion configuration to a second configuration in which the embolic material blocking element is in a deployed configuration, and from the second configuration to a third configuration in which the embolic material blocking element is in a captured configuration, the first configuration accommodating insertion of the distal portion of the elongated element and the embolic material blocking element into the aorta downstream of an implantation site for the prosthetic aortic valve, the deployed configuration of the embolic material blocking element having an outer circumference adapted to interface with the inner surface of the aorta and substantially blocking flow of embolic material through the aorta past the embolic material blocking element, the third configuration accommodating removal of the distal portion of the elongated element and the embolic material blocking element from the patient;
   an insertion port configured to accommodate insertion of a distal portion of a delivery catheter supporting the prosthetic valve into the lumen of the elongated element and advancement of the distal portion of the delivery catheter through the lumen to position the prosthetic aortic valve upstream of the embolic material blocking element, the insertion port being configured to inhibit leakage from the lumen; and a delivery catheter configured to deploy the prosthetic aortic valve, the delivery catheter being configured to be advanced through the lumen of the elongated element of the embolic material blocking catheter to position the prosthetic aortic valve upstream of the embolic material blocking element for deployment, the delivery catheter including a deployment mechanism adapted to deploy the prosthetic aortic valve from a pre-deployment configuration.

2. The system of claim 1, wherein the deployment mechanism comprises an expandable member configured to deploy the prosthetic aortic valve by expanding the prosthetic aortic valve from the pre-deployment configuration.

3. The system of claim 1, wherein the embolic material blocking catheter comprises an articulable sheath repositionable from:
  a first position adapted to retain the embolic material blocking element in the insertion configuration to a second position accommodating the embolic material blocking element in the deployed configuration; and
  the second position to a third position restraining the embolic material blocking element in the captured configuration.

4. The system of claim 1, wherein the embolic material blocking element comprises a filtering membrane adapted to remove embolic material from blood flowing through the aorta.

5. The system of claim 1, wherein:
  the handle assembly includes an embolic material extraction port in fluid communication with the lumen of the elongated element;
  the lumen of the elongated element is configured to transport embolic material that is diverted by the embolic material blocking element to the embolic material extraction port; and
  the embolic material extraction port is configured to be placed in fluid communication with an embolic material extraction device operable to draw embolic material from the lumen through the embolic material extraction port.

6. The system of claim 5, wherein the embolic material blocking element is configurable to extend downstream from an outer circumference of the embolic material blocking element to an inner circumference of the embolic material blocking element coupled with the elongated element so as to guide embolic material diverted by the embolic material blocking element to the lumen of the elongated element for transport through the lumen for removal via the embolic material extraction port.

7. The system of claim 1, wherein the embolic material blocking element extends proximally from the inner circumferential portion to an outer circumferential portion of the embolic material blocking element in the insertion configuration.

8. The system of claim 1, wherein the embolic material blocking catheter is reconfigurable to reconfigure the embolic material blocking element from the insertion configuration to an intermediate deployment configuration, the embolic material blocking element having a substantially flat disk shape in the intermediate deployment configuration, the embolic material blocking element having a substantially cone-shaped configuration in the fully deployed configuration, the embolic material blocking element being reconfigurable from the intermediate deployment configuration to the fully deployed configuration via a proximal retraction of the embolic material blocking catheter with an outer circumferential portion of the embolic material blocking element interfaced with the aorta so as to deform the embolic material blocking element from the intermediate deployment configuration to the fully deployed configuration.

* * * * *